(12) United States Patent
Gershoni et al.

(10) Patent No.: US 8,715,684 B2
(45) Date of Patent: May 6, 2014

(54) PEPTIDES INDUCING A CD4I CONFORMATION IN HIV GP120 WHILE RETAINING VACANT CD4 BINDING SITE

(75) Inventors: Jonathan M. Gershoni, Herzliya (IL); Gal Dela, Kiryat Ono (IL)

(73) Assignee: Ramot at Tel Aviv University Ltd., Tel Aviv (IL)

( * ) Notice: Subject to any disclaimer, the term of this patent is extended or adjusted under 35 U.S.C. 154(b) by 730 days.

(21) Appl. No.: 12/675,334

(22) PCT Filed: Aug. 28, 2008

(86) PCT No.: PCT/US2008/074634
§ 371 (c)(1),
(2), (4) Date: Feb. 25, 2010

(87) PCT Pub. No.: WO2009/029716
PCT Pub. Date: Mar. 5, 2009

(65) Prior Publication Data
US 2010/0247558 A1    Sep. 30, 2010

Related U.S. Application Data

(60) Provisional application No. 60/968,521, filed on Aug. 28, 2007.

(51) Int. Cl.
*A61K 39/21* (2006.01)
*A61K 38/00* (2006.01)
*A61K 38/04* (2006.01)

(52) U.S. Cl.
USPC .............. 424/188.1; 424/208.1; 530/326; 530/327; 530/328

(58) Field of Classification Search
None
See application file for complete search history.

(56) References Cited

U.S. PATENT DOCUMENTS

| 5,556,744 A | 9/1996 | Weiner et al. |
| 2009/0075832 A1 | 3/2009 | Neuman et al. |

FOREIGN PATENT DOCUMENTS

| WO | 0116182 A | 3/2001 |
| WO | 2006091734 A | 8/2006 |

OTHER PUBLICATIONS

Gallo, R. C., 2005, The end or the beginning of the drive to an HIV-preventive vaccine: a view from over 20 years, The Lancet 366:1894-1898.*
Lin, G., and P. Nara, 2007, Designing immunogens to elicity broadly neutralizing antibodies to the HIV-1 envelope glycoprotein, Current HIV Research 5:514-541.*
McElrath, M. J., and B. F. Haynes, 2010, Induction to immunity to human immunodeficiency virus type-1 by vaccination, Immunity 33:542-554.*
Walker, B. D., and D. R. Burton, 2008, Toward an AIDS vaccine, Science 320:760-764.*
Ferrer et al.,"Peptide Ligands to Human Immunodeficiency Virus Type 1 GP 120 Identified From Phage Display Libraries," Journal of virology, 1999, pp. 5795-5802, vol. 73, No. 7, the American Society for Microbiology, US.

* cited by examiner

*Primary Examiner* — Jeffrey Parkin
(74) *Attorney, Agent, or Firm* — Browdy and Neimark, PLLC

(57) ABSTRACT

A novel peptides are complexed with HIV-I envelope protein gp120, and causes the protein to assume a CD4i conformation but without occluding the CD4 binding-site of gp120. This peptide-gp120 complex is immunogenic and, upon immunization of subjects, induces broadly-neutralizing antibodies directed to the CD4 binding site of gp120. The peptide preferably consists of a sequence of 8-20 amino acid residues which comprises (a) a core sequence Arg-$Xaa_1$-Asp-Leu-Pro-$Xaa_2$-Trp-Ala (SEQ ID NO: 1) in which $Xaa_1$ and $Xaa_2$ is any amino acid, or (b) certain substitution variants of SEQ ID NO:1.

10 Claims, 3 Drawing Sheets

SEQUENCE LISTING

```
<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa may be any amino acid
<220> FEATURE:
<221> NAME/KEY: misc_feature
<222> LOCATION: (6)..(6)
<223> OTHER INFORMATION: Xaa may be any amino acid

<400> SEQUENCE: 1

Arg Xaa Asp Leu Pro Xaa Trp Ala
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa may be any amino acid
<220> FEATURE:
<221> NAME/KEY: misc_feature
```

```
<222> LOCATION: (3)..(3)
<223> OTHER INFORMATION: Xaa may be any amino acid
<220> FEATURE:
<221> NAME/KEY: misc_feature
<222> LOCATION: (7)..(7)
<223> OTHER INFORMATION: Xaa may be any amino acid

<400> SEQUENCE: 2

Xaa Arg Xaa Asp Leu Pro Xaa Trp Ala
1               5

<210> SEQ ID NO 3
<211> LENGTH: 14
<212> TYPE: PRT
<213> ORGANISM: Artificial Sequence
<220> FEATURE:
<223> OTHER INFORMATION: synthetic

<400> SEQUENCE: 3

Cys Asp Arg Arg Asp Leu Pro Gln Trp Ala Lys Arg Glu Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic

<400> SEQUENCE: 4

Cys Asp Arg Ser Asp Leu Pro Gln Trp Ala Lys Arg Ala Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic

<400> SEQUENCE: 5

Cys Gly Arg Arg Asp Leu Pro Lys Trp Ala Met Arg Glu Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic

<400> SEQUENCE: 6

Cys Asp Arg Arg Asp Leu Pro Glu Trp Ala Lys Arg Glu Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic

<400> SEQUENCE: 7

Cys Asp Arg Arg Asp Leu Pro Gln Trp Ala Ile Arg Glu Cys
1               5                   10

<210> SEQ ID NO 8
<211> LENGTH: 14
```

```
<212> TYPE: PRT
<213> ORGANISM: Artificial Sequence
<220> FEATURE:
<223> OTHER INFORMATION: synthetic

<400> SEQUENCE: 8

Cys Ala Arg Arg Asp Leu Pro Leu Trp Ala Lys Arg Glu Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic

<400> SEQUENCE: 9

Cys Asp Arg Asn Asp Leu Pro Gln Trp Ala Lys Ser Ala Cys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: synthetic

<400> SEQUENCE: 10

Cys Asp Arg Arg Asp Leu Pro Gln Trp Ala Asn Arg Ala Cys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: synthetic

<400> SEQUENCE: 11

Cys Asp Arg Arg Asp Leu Pro Gln Trp Ala Met Ser Ala Cys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: synthetic

<400> SEQUENCE: 12

Cys Asp Arg Arg Asp Leu Pro Gln Trp Ala Ile Ser Ala Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic

<400> SEQUENCE: 13

Cys Asp Arg Ser Asp Leu Pro Gln Trp Ala Ile Ser Ala Cys
1               5                   10

<210> SEQ ID NO 14
<211> LENGTH: 14
<212> TYPE: PRT
<213> ORGANISM: Artificial Sequence
```

```
<220> FEATURE:
<223> OTHER INFORMATION: synthetic

<400> SEQUENCE: 14

Cys Asp Arg Arg Asp Leu Pro Gln Trp Ala Ile Ser Val Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetic

<400> SEQUENCE: 15

Cys Asp Arg Arg Asp Leu Pro Asp Trp Ala Ile Arg Ala Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa is Glu, Gly or Ala
<220> FEATURE:
<221> NAME/KEY: misc_feature
<222> LOCATION: (4)..(4)
<223> OTHER INFORMATION: Xaa is Asp, Ser or Asn
<220> FEATURE:
<221> NAME/KEY: misc_feature
<222> LOCATION: (8)..(8)
<223> OTHER INFORMATION: Xaa is Gln, Lys, Leu, Asp or Glu
<220> FEATURE:
<221> NAME/KEY: misc_feature
<222> LOCATION: (11)..(11)
<223> OTHER INFORMATION: Xaa is Lys, Ile, Met or Asn
<220> FEATURE:
<221> NAME/KEY: misc_feature
<222> LOCATION: (12)..(12)
<223> OTHER INFORMATION: Xaa is Arg or Ser
<220> FEATURE:
<221> NAME/KEY: misc_feature
<222> LOCATION: (13)..(13)
<223> OTHER INFORMATION: Xaa is Glu, Ala or Val

<400> SEQUENCE: 16

Cys Xaa Arg Xaa Asp Leu Pro Xaa Trp Ala Xaa Xaa Xaa Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa is Glu, Gly or Ala
<220> FEATURE:
<221> NAME/KEY: misc_feature
<222> LOCATION: (4)..(4)
<223> OTHER INFORMATION: Xaa is Asp, Ser or Asn
<220> FEATURE:
<221> NAME/KEY: misc_feature
<222> LOCATION: (8)..(8)
<223> OTHER INFORMATION: Xaa is Gln, Lys, Leu, Asp or Glu
<220> FEATURE:
<221> NAME/KEY: misc_feature
<222> LOCATION: (11)..(11)
```

```
<223> OTHER INFORMATION: Xaa is Lys, Ile, Met or Asn
<220> FEATURE:
<221> NAME/KEY: misc_feature
<222> LOCATION: (12)..(12)
<223> OTHER INFORMATION: Xaa is Arg or Ser
<220> FEATURE:
<221> NAME/KEY: misc_feature
<222> LOCATION: (13)..(13)
<223> OTHER INFORMATION: Xaa is Glu, Ala or Val

<400> SEQUENCE: 17

Glu Xaa Arg Xaa Asp Leu Pro Xaa Trp Ala Xaa Xaa Xaa Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa is Glu, Gly or Ala
<220> FEATURE:
<221> NAME/KEY: misc_feature
<222> LOCATION: (4)..(4)
<223> OTHER INFORMATION: Xaa is Arg, Ser or Asn
<220> FEATURE:
<221> NAME/KEY: misc_feature
<222> LOCATION: (8)..(8)
<223> OTHER INFORMATION: Xaa is Gln, Lys, Leu, Asp or Glu
<220> FEATURE:
<221> NAME/KEY: misc_feature
<222> LOCATION: (11)..(11)
<223> OTHER INFORMATION: Xaa is Lys, Ile, Met or Asn
<220> FEATURE:
<221> NAME/KEY: misc_feature
<222> LOCATION: (12)..(12)
<223> OTHER INFORMATION: Xaa is Arg or Ser
<220> FEATURE:
<221> NAME/KEY: misc_feature
<222> LOCATION: (13)..(13)
<223> OTHER INFORMATION: Xaa is Glu, Ala or Val

<400> SEQUENCE: 18

Lys Xaa Arg Xaa Asp Leu Pro Xaa Trp Ala Xaa Xaa Xaa Glu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic

<400> SEQUENCE: 19

Glu Asp Arg Arg Asp Leu Pro Asp Trp Ala Ile Arg Ala Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: synthetic

<400> SEQUENCE: 20

Lys Asp Arg Arg Asp Leu Pro Asp Trp Ala Ile Arg Ala Glu
1               5                   10

<210> SEQ ID NO 21
```

```
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa is preferably Arg, Lys, Ser, Asn or Leu
<220> FEATURE:
<221> NAME/KEY: misc_feature
<222> LOCATION: (6)..(6)
<223> OTHER INFORMATION: Xaa is preferably Gln, Glu, Lys, Leu, Asp, or
      Asn

<400> SEQUENCE: 21

Arg Xaa Asp Leu Pro Xaa Trp Ala
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa is any amino acid
<220> FEATURE:
<221> NAME/KEY: misc_feature
<222> LOCATION: (3)..(3)
<223> OTHER INFORMATION: Xaa is preferably Asp, Gly or Ala
<220> FEATURE:
<221> NAME/KEY: misc_feature
<222> LOCATION: (7)..(7)
<223> OTHER INFORMATION: Xaa is any amino acid

<400> SEQUENCE: 22

Xaa Arg Xaa Asp Leu Pro Xaa Trp Ala
1               5
```

US 8,715,684 B2

PEPTIDES INDUCING A CD4I CONFORMATION IN HIV GP120 WHILE RETAINING VACANT CD4 BINDING SITE

BACKGROUND OF THE INVENTION

1. Field of the Invention

The invention in the field of biochemistry and immunology relates to novel peptides that induce and stabilize an immunogenic conformation in HIV-1 gp120 protein, and thereby provide compositions useful in a method for preventing or treating HIV infection.

2. Description of the Background Art

The failure of the VaxGen vaccine trial has convincingly dismissed the notion that simple recombinant monomeric HIV-1 gp120 proteins are sufficiently effective immunogens for AIDS vaccines. A clear consensus exists that induction of neutralizing antibodies will be an important feature of a successful AIDS vaccine, and that the most effective immunogen able to elicit these antibodies will have to contain some form of gp120. See, for example, Burton D R, 1997, *Proc Natl Acad Sci USA*. 94:10018-23; Burton D R, 2002, *Nat Rev Immunol.* 2:706-13; Zolla-Pazner S, 2004, *Nat Rev Immunol.* 4:199-210).

Therefore, the goal of many laboratories has been to produce more effective presentations of gp120 that could selectively induce the production of neutralizing antibodies. HIV gp120 can assume a conformation that reveals or stabilizes distinct epitopes that are able to elicit cross reactive neutralizing antibodies, and as such, represents a preferred presentation of the viral envelope to be used in a commercially useful prophylactic AIDS vaccine. Such a conformation of the viral envelope is induced when the envelope is complexed with CD4 (Thali, M et al., 1993, *J Virol* 67:3978-88; Kang, C Y et al., 1994, *J Virol* 68:5854-62; Sullivan, N et al., 1998, *J Virol* 72:4694-703; Xiang, S et al., 2003, *Virology* 315:124-34; DeVico, A L et al., 1995, *Virology* 211:583-8; Gershoni, J M et al., 1993, *FASEB J* 7:1185-7) leading to epitopes that have been referred to as CD4 induced ("CD4i") epitopes.

The problem, however, is that association of gp120 with CD4, by definition, occupies and thereby obscures, the CD4 binding-site (CD4BS) of the virus, forfeiting a highly effective neutralizing epitope. Moreover, efforts to induce CD4i in the absence of CD4, e.g., by mutagenesis (Xiang, S H et al., 2002, *J Virol* 76:9888-99) came at the expense of losing credible neutralizing epitopes such as that of mAb b12. This led some investigators to conclude that the conformation of CD4i and CD4BS are mutually exclusive.

Since a study published in 1990 (Celada, F et al., 1990, *J Exp Med* 172:1143-50), there has been continuous growing interest in the CD4/gp120 complex as an immunogen. Originally, the intent was to identify novel sites on CD4 possibly involved in viral entry (Celada et al., supra) but by 1993 it was appreciated that the viral receptor might be able to lock gp120 into a preferred conformation, thereby revealing novel epitopes that have since become known as CD4i epitopes of the envelope. See also J. M. Gershoni, Int'l Pat. Publ., WO9415638A1, published Jul. 21, 1994.

The CD4i conformation of gp120 is operationally defined by the binding of mAbs that show a distinct preference for CD4-complexed gp120 as compared to free gp120. Examples of such defining antibodies are the murine mAbs CG10 (Gershoni et al., 1993, supra; Gershoni, 1994, supra) and 8F101 (DeVico et al., supra) and the human mAbs 17b, 48d (Thali et al., supra) and E51 (Xiang et al., 2003, supra). CD4i epitopes have been equated with the co-receptor binding site on gp120 (Xiang, S H et al., 2002, *AIDS Res Hum Retroviruses* 18:1207-17) and, as such, are perceived as potential vaccine candidates. This is based on the idea that CD4i epitopes represent relatively conserved epitopes of gp120 that become better exposed or immunogenic when the virus binds to CD4.

Subsequently, chemically cross linked versions of CD4/gp120 were shown to elicit neutralizing antibodies in goats and monkeys (Devico, A et al., 1996, *Virology* 218:258-63; Fouts, T et al., 2002, *Proc Natl Acad Sci USA* 99:11842-7). There is disagreement as to whether the neutralizing activity is actually due to anti-gp120 or rather to anti-CD4 antibodies (Varadarajan, R et al., 2005, *J Virol* 79, 1713-23).

If it were possible to replace CD4 with an alternative mimetic, then issues of anti-CD4 autoimmunity would be circumvented. To this end, modified scorpion toxins were examined and found to function as alternative molecules that could, upon binding to gp120, induce the CD4i conformation (Vita, C et al., 1999, *Proc Natl Acad Sci USA* 96:13091-6; Huang, C C et al., 2005, *Structure* 13:755-68). DNA encoding either D1-D2 domains of CD4 or the scorpion toxin mimetics were spliced with gp120-encoding DNA to create a single chain gene that encodes a protein with two components of the complex folded in a manner that allows them to bind to each other (Fouts, T R et al., 2000, *J Virol* 74:11427-36; He, Y., D'Agostino, P et al., 2003, *Vaccine* 21:4421-9).

Several other approaches to stabilize gp120 in a preferred conformation have been devised. Three possibilities for this are (1) modifying the repertoire of sugar moieties of the glycoprotein to accentuate the desired accessible surfaces of gp120 (Pantophlet, R et al., 2003, *J Virol* 77:5889-901), (2) complexing gp120 with unique antibodies that induce CD4i conformation (Liao, H X et al., 2004, *J Virol* 78:5270-8; Wyatt, R et al., 1995, *J Virol* 69:5723-33); or (3) introducing strategically placed mutations to fix gp120 into the desired configuration (Xiang, S H, 2002, supra; Yang, X et al., 2000, *J Virol* 74:4746-54).

A case in point for the latter approach was the introduction of the mutation 375 S/W in gp120 with the intention of locking gp120 into the CD4i conformation, postulating that a Trp residue at position 375 would effectively simulate the Phe at position 43 of CD4. Whereas this mutation induced the 17b epitope in gp120 (i.e., induced binding to mAb 17b, a "marker" of the CD4i conformation), the structure simultaneously lost the b12 epitope which overlaps the CD4BS. It was concluded that the CD4BS conformation (represented by an intact b12 epitope) and the CD4i conformation (represented by 17b binding) are distinct, different and mutually exclusive.

MAb A32 has been used to induce CD4i, and this complex was tested as an immunogen (Liao et al., supra). Whereas A32 complexed with gp120$_{89.6}$ produced more neutralizing antibodies than gp120$_{89.6}$ alone, this property was not found for the A32/gp120$_{BaL}$ complex. It was concluded that monomeric gp120$_{BaL}$, rather than a complex, was the best immunogen of those tested.

Therefore, a well-recognized need remains to overcome the deficits in the prior art described above. The present invention is intended to provide novel solutions to such problems.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to a peptide that binds to HIV-1 envelope protein gp120, and preferably consists of a sequence of 8-20 amino acid residues which peptide, when bound to gp120, causes the gp120 to assume a CD4i conformation.

In a preferred embodiment, the above peptide consists of a sequence of 8-20 amino acid residues which sequence comprises:

(a) a core sequence Arg-$Xaa_1$-Asp-Leu-Pro-$Xaa_2$-Trp-Ala (SEQ ID NO:1) wherein $Xaa_1$ and $Xaa_2$ may be any amino acid, or (b) a peptide variant of SEQ ID NO:1 in which one or more, preferably no more than three, of the residues Arg, Asp, Leu, Pro, Trp and Ala is conservatively substituted.

$Xaa_1$ is preferably Arg, Lys, Ser, Asn or Leu. $Xaa_2$ is preferably Gln, Glu, Lys, Leu, Asp, or Asn.

When bound to gp120, the above peptide causes the gp120 to assume a CD4i conformation. The substitutions discussed herein must be chosen such that this function is retained.

When the above peptide binds to gp120, the peptide-gp120 complex binds to CD4 or a gp120-binding fragment or variant of CD4. Moreover, in a preferred embodiment, the peptide-gp120 complex retains functional epitopes of the CD4 binding site (a "CD4BS epitope") of gp120 and continues to bind to mAbs such as b12. Stated another way, the preferred embodiment of the above peptide is one that binds to gp120 without substantially interfering with binding of the gp120 to (a) CD4 or a gp120-binding fragment or variant of CD4; or (b) a mAb or other ligand specific for a CD4BS epitope of gp120. Preferably, the substitutions discussed herein are chosen such that these functions are retained.

A preferred peptide is as above comprises SEQ ID NO:1, wherein $Xaa_1$ is Arg, Lys, Ser, Asn or Leu and $Xaa_2$ is Gln, Glu, Lys, Leu, Asp, or Asn (SEQ ID NO:21).

A preferred peptide extends the above core sequence further by addition of an N-terminal $Xaa_3$ to the first (N-terminal) residue of SEQ ID NO:1, so that this extended peptide comprises $Xaa_3$-Arg-$Xaa_1$-Asp-Leu-Pro-$Xaa_2$-Trp-Ala (SEQ ID NO:2) wherein $Xaa_3$ is any amino acid, preferably Asp, Gly or Ala (SEQ ID NO:22).

In another preferred embodiment, the above peptide, when complexed with (i) gp120, or (ii) a fragment or variant of the gp120 that binds the peptide, binds to CD4i specific monoclonal antibodies such as the human mAb 17b and/or the murine mAb CG10.

In a preferred embodiment, the length of the above peptide is 12-20 residues, and comprises two Cys residues that are separated by at least 10 residues. Alternatively, the peptide consists of 14 to 20 residues and includes two Cys residues separated by 12-14 residues.

A preferred example of such a peptide is (SEQ ID NO: 16)
Cys-$Xaa_3$-Arg-$Xaa_1$-Asp-Leu-Pro-$Xaa_2$-Trp-Ala-$Xaa_4$-$Xaa_5$-$Xaa_6$-Cys wherein $Xaa_1$ is Arg, Ser or Asn $Xaa_2$ is Gln, Lys, Leu, Asp or Glu;

$Xaa_3$ is Asp, Gly or Ala $Xaa_4$ is Lys, Ile, Met or Asn;

$Xaa_5$ is Arg or Ser; and $Xaa_6$ is Glu, Ala or Val.

A more preferred peptide is selected from the group consisting of:

(SEQ ID NO: 3)
(a) Cys-Asp-Arg-Arg-Asp-Leu-Pro-Gln-Trp-Ala-Lys-Arg-Glu-Cys (SEQ ID NO: 4)
(b) Cys-Asp-Arg-<u>Ser</u>-Asp-Leu-Pro-Gln-Trp-Ala-Lys-Arg-<u>Ala</u>-Cys;

(SEQ ID NO: 5)
(c) Cys-<u>Gly</u>-Arg-Arg-Asp-Leu-Pro-<u>Lys</u>-Trp-Ala-<u>Met</u>-Arg-Glu-Cys;

(SEQ ID NO: 6)
(d) Cys-Asp-Arg-Arg-Asp-Leu-Pro-<u>Glu</u>-Trp-Ala-Lys-Arg-Glu-Cys;

(SEQ ID NO: 7)
(e) Cys-Asp-Arg-Arg-Asp-Leu-Pro-Gln-Trp-Ala-<u>Ile</u>-Arg-Glu-Cys;

(SEQ ID NO: 8)
(f) Cys-<u>Ala</u>-Arg-Arg-Asp-<u>Leu</u>-Pro-Leu-Trp-Ala-Lys-Arg-Glu-Cys;

(SEQ ID NO: 9)
(g) Cys-Asp-Arg-<u>Asn</u>-Asp-Leu-Pro-Gln-Trp-Ala-Lys-<u>Ser</u>-<u>Ala</u>-Cys;

(SEQ ID NO: 10)
(h) Cys-Asp-Arg-Arg-Asp-Leu-Pro-Gln-Trp-Ala-<u>Asn</u>-Arg-<u>Ala</u>-Cys;

(SEQ ID NO: 11)
(i) Cys-Asp-Arg-Arg-Asp-Leu-Pro-Gln-Trp-Ala-<u>Met</u>-<u>Ser</u>-<u>Ala</u>-Cys;

(SEQ ID NO: 12)
(j) Cys-Asp-Arg-Arg-Asp-Leu-Pro-Gln-Trp-Ala-<u>Ile</u>-<u>Ser</u>-<u>Ala</u>-Cys;

(SEQ ID NO: 13)
(k) Cys-Asp-Arg-<u>Ser</u>-Asp-Leu-Pro-Gln-Trp-Ala-<u>Ile</u>-<u>Ser</u>-<u>Ala</u>-Cys;

(SEQ ID NO: 14)
(l) Cys-Asp-Arg-Arg-Asp-Leu-Pro-Gln-Trp-Ala-<u>Ile</u>-<u>Ser</u>-<u>Val</u>-Cys;
and (SEQ ID NO: 15)
(m) Cys-Asp-Arg-Arg-Asp-Leu-Pro-<u>Asp</u>-Trp-Ala-<u>Ile</u>-Arg-<u>Ala</u>-Cys, wherein the underscored residues are substitutions in the peptide which is also designated m1 (SEQ ID NO:3).

A most preferred peptide is the peptide designated m2, the sequence of which is SEQ ID NO:15.

Another embodiment of this invention is a cyclic form of the above peptide wherein the two Cys residues are linked in a disulfide bond.

Alternatively, the peptide is one with a length of 12-20 residues, wherein the sequence further comprises a first and a second amino acid residue or other cyclizing moiety that is not a conventional amino acid, that can, upon binding to one another, result in the cyclization of the peptide backbone while retaining the peptide's desired biochemical properties as disclosed herein. Backbone cyclization methods of Gilon C et al., 1991, *Biopolymers* 31:745-50 (see also related citations below) can be employed, where additional reactive groups that are used to cross-link the backbone are introduced without involving the amino acid's natural R groups (side chains).

Thus, according to this invention, a cyclized peptide results from cyclization due to bonding between amino acid residues other than Cys and possibly involving atoms that are not part of the amino acids' R groups. The cyclizing residues are separated from one another by at least 10 residues, or, preferably, by 12-14 residues. Preferred examples of such peptides are ones in which (a) the first cyclizing residue is Glu and the second cyclizing residue is Lys; or (b) the first cyclizing residue is Lys and the second cyclizing residue is Glu, wherein cyclization is achieved by linking the carboxyl side chain of the Glu residue with the amino side chain of the Lys residue. Preferred peptides of this type are

```
                                              (SEQ ID NO: 17)
(a) Glu-Xaa₃-Arg-Xaa₁-Asp-Leu-Pro-Xaa₂-Trp-Ala-
Xaa₄-Xaa₅-Xaa₆-Lys;
or
                                              (SEQ ID NO: 18)
(b) Lys-Xaa₃-Arg-Xaa₁-Asp-Leu-Pro-Xaa₂-Trp-Ala-
Xaa₄-Xaa₅-Xaa₆-Glu.
``` wherein
Xaa₁ is Arg, Ser or Asn
Xaa₂ is Gln, Lys, Leu, Asp or Glu;
Xaa₃ is Asp, Gly or Ala
Xaa₄ is Lys, Ile, Met or Asn;
Xaa₅ is Arg or Ser; and
Xaa₆ is Glu, Ala or Val.

Most preferred peptides of this type are based on the sequence of m2:

```
                                              (SEQ ID NO: 19)
(a) Glu-Asp-Arg-Arg-Asp-Leu-Pro-Asp-Trp-Ala-Ile-
Arg-Ala-Lys;
or
                                              (SEQ ID NO: 20)
(b) Lys-Asp-Arg-Arg-Asp-Leu-Pro-Asp-Trp-Ala-Ile-
Arg-Ala-Glu.
```

The above peptide may comprise D-amino acids or, as noted, unnatural amino acids that have the advantage of providing sites for cross-linking and stabilization of the complexes. Such approaches are well-known in the art. Once again, technology using synthetic conformers of the peptides may also be employed. See for example, Gilon et al., 1991, supra; Kasher R et al., 1999, *J Mol Biol.* 292:421-9; Fridkin G et al., 2005, *Nucl Med Biol.* 32:39-50; Koch Y, 2006, *J Pept Sci.* 12:106-15, which are hereby incorporated by reference in their entirety.

It should be understood that as long as the peptide described above binds to gp120 and induces the CD4i structure without occluding CD4 binding sites, it is within the scope of this invention. Without undue experimentation, one may readily screen panels of peptide variants, or libraries of conformers or variants as disclosed herein to identify peptides, preferably derived from and modified from m1 (SEQ ID NO:3) and m2 (SEQ ID NO:15) that retain the desired biochemical and biological properties of m1 and m2 as described, namely, binding to gp120 and induction of CD4i. The sequence of new molecules identified in this way may have deviated from that of m1 or m2, and may include, as noted above, D-amino acids, non-natural amino acids, or even organic moieties that are not in sensu strictu amino acids. What is important is that they maintain the same binding properties noted above. Clearly, such a molecule would retain a significant degree of semblance, in terms of its 3D structure, to m1 or m2.

Also provided herein is a linear oligomer or multimer that comprises between about two and about 20 repeats of the above linear peptides. This construct may optionally include one or more linker peptides, each of which is placed between two adjacent repeating units.

The oligomer or multimer may be cyclized.

Also included is a tandem oligomeric peptide that comprises two or three repeats of the above peptide that are linked in tandem ("side-by-side").

A preferred oligomer/multimer is a dendritic "polymer" or dendrimer built on a core molecule which is at least bifunctional so as to provide branching and contains up to about 16 terminal functional groups to each of which is covalently linked a peptide as described above.

The present invention is also directed to a molecular complex that comprises gp120 bound or linked to a peptide as described above, or linked to the linear or cyclized oligomer or multimer or the tandem oligomer. In one embodiment, the gp120 is bound or linked to the dendritic polymer. In the above molecular complex, the peptide may be linked to gp120 by a flexible linker.

In one preferred complex, the peptide and the gp120 are linked in a linear manner.

Such a complex is preferably encoded by a single, linear polynucleotide, preferably DNA, sequence.

In the complexes described herein, the peptide may be chemically cross-linked to gp120.

In the preferred complex, the peptide or the gp120 is presented in a multivalent manner while retaining the property that the CD4i conformation of CD4 is "locked".

In one embodiment of the multivalent complex, the peptide is linked to a filamentous bacteriophage. The complex may also be linked to a dendritic polymer.

In the foregoing complexes, a preferred gp120 molecule is the gp120 from the HIV-1 strain BaL (gp120$_{BaL}$).

A most preferred complex comprises the peptide

```
                                              (SEQ ID NO: 15)
Cys-Asp-Arg-Arg-Asp-Leu-Pro-Asp-Trp-Ala-Ile-Arg-
Ala-Cys
```

This invention also provides an immunogenic composition comprising
(a) a complex as above wherein binding of the peptide to gp120 causes gp120 to assume the CD4i conformation; and
(b) a pharmaceutically and immunologically acceptable carrier.

The immunogenic composition may also further comprise an immunostimulatory factor or agent, such as an adjuvant.

The present invention is also directed to a DNA molecule encoding a linear peptide as described above or a linear oligomer or multimer, or a molecular complex, as described.

Also included is an expression vector comprising the above DNA molecule that is operatively linked to a promoter and, optionally, one of more transcriptional regulatory sequences that promote expression of the DNA in an intended cell or subject.

In addition, the invention provides a method of treating a subject infected with HIV, comprising administering to the subject an effective amount of a composition comprising the peptide as described above, or the peptide oligomer, multimer or dendritic polymer.

Also provided is a method of treating a subject infected with HIV, comprising administering to the subject an effective amount of a composition comprising the above molecular complex, preferably an effective amount of an immunogenic composition as above.

In another embodiment, the method of preventing or treating HIV infection in a subject comprises administering a DNA molecule described above which DNA molecule is expressible in, and expressed in, the subject after administration.

The invention is further directed to an HIV-specific antiserum, an enriched immunoglobulin fraction thereof, or isolated antibodies from the serum or immunoglobulin fraction, obtained from a subject or subjects who have been immunized with:

(a) an immunogen comprising the peptide as above;
(b) an immunogen comprising the oligomer, multimer or dendritic polymer as above;
(c) the molecular complex as above; or
(d) the immunogenic composition described above;
(e) a DNA molecule as described above which is expressed in the subject after administration.

The present invention is also directed to a method of identifying a peptide that can be used as part of an anti-HIV immunogen. The method comprises screening a library or collection of peptides for a peptide that (a) binds to gp120, (b) induces the CD4i conformation in the gp120 protein, (c) maintains the CD4BS epitopes, and (d) keeps the CD4 binding site of gp120 vacant and available for binding to CD4 or a gp120 binding fragment or homologue of CD4.

The library may be a phage peptide library. The first step of the screening is preferably binding to selected gp120. Once bound, the peptides/gp120 complex is screened or probed with a mAb that recognizes the CD4i structure, preferably mAb 17b or CG10 which are specific for CD4-complexed gp120. The peptide that passes through these steps is then obtained in isolated form. Of peptides identified and isolated using this method, one, designated m1 (SEQ ID NO:3) bound gp120$_{451}$ and promoted CG10 binding. m1 peptide and CD4 were found to bind simultaneously to gp120. This was the first demonstration of actual stabilization of the CD4i conformation of gp120 (as defined by CG10 binding) while retaining a vacant and functionally accessible CD4 binding site simultaneous with accessible CD4BS epitopes.

In the present method, the peptides identified and/or isolated in this manner may be further optimized, for example, for a gp120 molecule from a particular clade or isolate of HIV. The gp120 target of the optimized peptide may be recombinant, and may include a consensus sequence of a selected region, e.g., one of the variable loops of gp120. This was done by the present inventors in their isolation of peptide m2 described in more detail herein, which is characterized by inducing this unique CD4i conformation in gp120 from the BaL isolate of HIV-1. As noted above, the present peptides, and any new peptide discovered using this method, is then complexed with the appropriate gp120 polypeptide and used as an immunogen to induce broadly reactive neutralizing antibodies.

DESCRIPTION OF THE PREFERRED EMBODIMENTS

Figure 1:
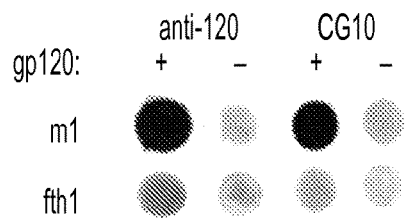
FIG. 1 shows that the m1 peptide (SEQ ID NO:3) binds gp120 and induces the CG10 epitope. Phages expressing the m1 peptide as protein fusions (m1) or not (fth1, as a negative control) were applied to nitrocellulose membranes as dots and incubated with or without gp120$_{451}$. After washing, the filters were probed with either anti-gp120 mAb or the CG10 mAb as indicated and signals were developed by enhanced chemiluminescence (ECL)

The present invention is directed to peptides that induce a novel stabilized transient conformation of HIV-1 gp120 designated "CD4i" that is exploited as an immunogen that induces broadly neutralizing antibodies against HIV-1, including antibodies directed to the CD4 binding site of HIV-1 envelope glycoprotein gp120. The preferred peptides of the present invention are described both generically (with alternative residues at certain positions, and specifically (one single sequence) in Table 1.

A preferred way to monitor the presence of such desired conformation is to test the binding of a CD4i-specific mAb, such as the human mAb 17b or the murine mAb CG10. Binding of 17b or CG10 serves to confirm that gp120 has assumed a conformation that is markedly different from that of the recombinant monomeric gp120 (which failed in the VaxGen trials when tested as a vaccine composition). It is known in the art that gp120 from certain HIV-1 isolates or strains binds, in the absence of complexed CD4, to a mAb that is otherwise characterized as a "marker" for the CD4i structure. An example is mAb 17b binding to gp120$_{451}$ without CD4 being present. In that case, mAb CG10 or yet another such mAb, the binding of which is strictly "CD4-dependent, can be used instead.

TABLE 1

| Name*Sequence | SEQ ID NO: |
|---|---|
|     1  2  3  4  5  6  7  8<br>    Arg-Xaa$_1$-Asp-Leu-Pro-Xaa$_2$-Trp-Ala<br>Xaa$_1$ is any aa, preferably Arg, Lys Ser, Asn or Leu, . more preferably Arg, Asn, Ser<br>Xaa$_2$ is any aa, preferably Gln, Lys, Glu, Leu, Asp | 1 |
|     1  2  3  4  5  6  7  8  9<br>    Xaa$_3$-Arg-Xaa$_1$-Asp-Leu-Pro-Xaa$_2$-Trp-Ala<br>Xaa$_1$ is any aa, preferably Arg, Asn, Ser<br>Xaa$_2$ is any aa, preferably Gln, Lys, Glu, Leu, Asp<br>Xaa$_3$ is preferably Gly, Asp, Ala | 2 |
| m1  1  2  3  4  5  6  7  8  9  10 11 12 13 14<br>    Cys-Asp-Arg-Arg-Asp-Leu-Pro-Glu-Trp-Ala-Lys-Arg-Glu-Cys | 3 |
| 2B-9 Cys-Asp-Arg-<u>Ser</u>-Asp-Leu-Pro-Gln-Trp-Ala-Lys-Arg-<u>Ala</u>-Cys* | 4 |
| 1D-3 Cys-<u>Gly</u>-Arg-Arg-Asp-Leu-Pro-<u>Lys</u>-Trp-Ala-<u>Met</u>-Arg-Glu-Cys | 5 |
| 2C-4 Cys-Asp-Arg-Arg-Asp-Leu-Pro-<u>Glu</u>-Trp-Ala-Lys-Arg-Glu-Cys | 6 |
| 2A-6 Cys-Asp-Arg-Arg-Asp-Leu-Pro-Gln-Trp-Ala-<u>Ile</u>-Arg-Glu-Cys | 7 |
| 1A-12 Cys-<u>Ala</u>-Arg-Arg-Asp-Leu-Pro-<u>Leu</u>-Trp-Ala-Lys-Arg-Glu-Cys | 8 |
| 2E-12 Cys-Asp-Arg-<u>Asn</u>-Asp-Leu-Pro-Gln-Trp-Ala-Lys-<u>Ser</u>-<u>Ala</u>-Cys | 9 |
| 1H-10 Cys-Asp-Arg-Arg-Asp-Leu-Pro-Gln-Trp-Ala-<u>Asn</u>-Arg-<u>Ala</u>-Cys | 10 |
| 4F-5 Cys-Asp-Arg-Arg-Asp-Leu-Pro-Gln-Trp-Ala-<u>Met</u>-<u>Ser</u>-<u>Ala</u>-Cys | 11 |
| 4F-4 Cys-Asp-Arg-Arg-Asp-Leu-Pro-Gln-Trp-Ala-<u>Ile</u>-<u>Ser</u>-<u>Ala</u>-Cys | 12 |
| 4F-12 Cys-Asp-Arg-<u>Ser</u>-Asp-Leu-Pro-Gln-Trp-Ala-<u>Ile</u>-<u>Ser</u>-<u>Ala</u>-Cys | 13 |
| 4B-6 Cys-Asp-Arg-Arg-Asp-Leu-Pro-Gln-Trp-Ala-<u>Ile</u>-<u>Ser</u>-<u>Val</u>-Cys | 14 |
| m2   Cys-<u>Asp</u>-<u>Arg</u>-<u>Arg</u>-<u>Asp</u>-Leu-Pro-<u>Asp</u>-Trp-Ala-Ile-<u>Arg</u>-Ala-Cys** | 15 |
|     1  2  3  4  5  6  7  8  9  10 11 12 13 14<br>    Cys-Xaa$_3$-Arg-Xaa$_1$-Asp-Leu-Pro-Xaa$_2$-Trp-Ala-Xaa$_4$-Xaa$_5$-Xaa$_6$-Cys<br>Xaa$_1$ is preferably Arg, Ser, Asn<br>Xaa$_2$ is preferably Gln, Lys, Leu, Asp, Glu<br>Xaa$_3$ is preferably Asp, Gly, Ala<br>Xaa$_4$ is preferably Lys, Ile, Met, Asn<br>Xaa$_5$ is preferably Arg or Ser<br>Xaa$_6$ is preferably Glu, Ala, Val | 16 |
|     *Glu*-Xaa$_3$-Arg-Xaa$_1$-Asp-Leu-Pro-Xaa$_2$-Trp-Ala-Xaa$_4$-Xaa$_5$-Xaa$_6$-*Lys* | 17 |
|     *Lys*-Xaa$_3$-Arg-Xaa$_1$-Asp-Leu-Pro-Xaa$_2$-Trp-Ala-Xaa$_4$-Xaa$_5$-Xaa$_6$-*Glu* | 18 |
|     *Glu*-Asp-Arg-Arg-Asp-Leu-Pro-Asp-Trp-Ala-Ile-Arg-Ala-*Lys* | 19 |
|     *Lys*-Asp-Arg-Arg-Asp-Leu-Pro-Asp-Trp-Ala-Ile-Arg-Ala-*Glu* | 20 |

*underscored = substitutions vs SEQ ID NO: 3;
**bold/underscored = readily derivatizable R group According to this invention, the complex between gp120 and the novel peptides of the invention, preferably the peptide m1 and m2 (described in more detail below), the major neutralizing gp120 epitopes, primarily the vacant CD4 binding site and epitopes thereof (referred to as "CD4BS" epitopes) gp120 (which are represented by mAb b12 binding), exist in a preferred presentation. Presented herein are results that confirm the foregoing by demonstrating that the m1-gp120 complex is bound very well by mAbs b12, b6, and m14 in addition to CG10 and 17b as well as soluble CD4.

Epitopes recognized by mAbs, as described herein, are sometimes referred to by the name of the mAb that defines them. Thus, for example, an epitope recognized by mAb b12 (and so on for other mAbs) is sometimes referred to herein as a "b12 epitope". Such a designation does not refer to an epitope that makes up a part of the structure of the mAb b12, but rather an epitope, primarily of the CD4 binding site of gp120, that is recognized and bound by the mAb.

The CD4i conformation of gp120 is operationally defined by the binding of mAbs that show a distinct preference for CD4 complexed gp120 as compared to gp120 alone. Examples of such defining antibodies are the murine mAbs CG10 (Gershoni et al., supra) and 8F101 (DeVico et al., supra) and the human mAbs 17b, 48d (Thali et al., supra) and E51(Xiang et al., 2003, supra).

The peptides of the present invention, such as the m2 peptide (described in more detail below as an improved substitution variant of the m1 peptide) are produced in larger, commercial quantities by solid phase chemical synthesis employing two independent approaches for loop formation. The peptides are used to produce complexes with available gp120 which can be subsequently tested for binding various ligands that define, and serve as "markers" of CD-4i. Examples of these ligands are soluble CD4 and a panel of "defining" mAbs including: CG10, 17b (CD4i) and CD4 binding site-specific Abs b12, b6 and m14.

The binding site of the m1 and m2 peptides is still not defined. It is known, however, that the peptide does not bind to the CD4 binding site of gp120, nor does its binding interfere with the CD4 binding site or the CD4BS epitopes recognized by CD4BS-specific mAb b12

The range of binding of the present peptides to various HIV-1 strains and isolates is not identical. For example, m1 binds to $gp120_{451}$ but not to $gp120_{JR\text{-}FL}$ (the gp120 of the JR-FL HIV-1 isolate). An improved peptide designated m2 also binds also to $gp120_{BaL}$ as well $gp120_{JR\text{-}FL}$. Since $gp120_{BaL}$ is a preferred immunogen (Pantophlet et al., supra), the m2-peptide/$gp120_{BaL}$ complex is preferred as an immunogen.

Xiang, S H et al., 2002, J Virol, supra), tested a series of gp120 mutants for their ability to lock gp120 into a CD4i conformation in the absence of CD4. Mutation 375 S/W was able to stabilize the CD4i conformation, albeit accompanied by the undesirable loss of b12 mAb binding. A second mutation, 423 I/P bound to b12 but lost mAb 17b binding. Therefore, the CD4i and CD4BS epitopes were concluded to be mutually exclusive, and this document stated: "These results indicate that CD4BS epitope antibodies recognize conformations of gp120 different from that recognized by CD4 and CD4i antibodies."

However, according to the present invention and based on results presented herein, the m1/gp120 complex is genuinely unique in that it binds both CD4i and CD4BS antibodies equally well. On this basis, the use of a selected m1/gp120 or m2-gp120 complex as an immunogen will induce antibodies specific to CD4i and CD4 binding site-specific antibodies, and thereby confer a state of protective or therapeutic immunity against HIV-1.

In Xiang et al., supra, locking gp120 into the CD4i conformation via mutation led to loss of b12 binding. However, the results presented below show that the m1/gp120 complex is a novel and distinct conformation of gp120 compatible with binding of (i) both classes of mAbs (those specific for CD4i and CD4BS epitopes) as well as (ii) soluble CD4. As an immunogen and vaccine the present immunogenic compositions comprising the peptide/gp120 complex will elicit antibodies to any one of these sites. There is no requirement that the induced antibodies bind to one and the same gp120 molecule simultaneously or cooperatively.

The present invention provides an alternative and better approach for locking gp120 into a CD4i conformation whilst leaving the CD4 binding site open. The present inventors have identified a short cyclizable peptide (m1) that elicits the CD4i conformation of $gp120_{451}$ without occluding the CD4 binding site. As described, the m1 peptide has been further optimized to yield the m2-peptide that locks $gp120_{BaL}$ into the CD4i conformation, maintains functional CD4BS epitopes as well as a free CD4 binding site per se.

The inventors' conception followed their use of mAbs that bound CD4i, particularly CG10, to "monitor" the presence of a preferred gp120 conformation that is distinct from the less effective native monomeric gp120. The preferred m2-peptide/$gp120_{BaL}$ complex is designed to present a free CD4 binding site and maintain the traditional CD4BS epitopes (e.g., b12) in addition to generation of CD4i epitopes that provide added value to the efficacy of this new immunogen.

gp120 is a dynamic protein that continually "samples" different conformational states and transitions (Pantophlet, R et al., 2006, Annu Rev Immunol 24:739-69; Pan, Y et al., 2005, J Mol Biol 350:514-27). Thus the CD4 binding site, CD4i epitopes and CD4BS epitopes are constantly being displayed with varying degrees of accessibility in the unliganded viral-associated gp120 trimer. Antibodies targeting the CD4 binding site or epitopes thereof will bind unliganded gp120 and block its interaction with cell surface CD4.

The present invention is directed to a novel presentation of gp120 which, by definition represents a transient state of the protein. In contrast to previously reported CD4/gp120 complexes or the mutated 375 S/W gp120, this novel presentation continues to bind CD4 and CD4BS mAbs in addition to the CD4i "markers."

The m1 peptide isolated by the present inventors on the basis of its binding to $gp120_{451}$ and induction of the CD4i conformation has several advantageous properties that distinguish it from CD4 itself, CD4 mimetics, or other compounds of the prior art. The m1 peptide binds gp120 well, induces the complexed conformation as illustrated by CG10 binding and surprisingly continues to bind CD4 as well as maintaining the classical CD4BS epitopes.

The m2 peptide has 10-fold higher affinity for gp120, binds $gp120_{BaL}$, and, like m1, induces the CD4i conformation, retention of a free CD4 binding site as well as CD4BS epitopes. The m2-peptide/$gp120_{BaL}$ complex is unique amongst the variety of envelope based vaccines that have been, and are being, tested. The ability of m2 to induce the changes in gp120 conformation to do without forfeiting the ultimate neutralizing epitopes, namely the CD4BS epitopes and the CD4 binding site itself on gp120, is the most advantageous feature of this peptide. This has been demonstrated using a preferred gp120 of the BaL viral isolate. Additional advantages of the present invention lie in the fact that the energetic cost of inducing the CD4i conformation (Myszka, D G et al., 2000, Proc Natl Acad Sci USA 97:9026-31; Kwong, P D et al., 2002, Nature 420:678-82) is paid for by m2 binding.

Therefore the CD4 binding site is presented in a more immunogenic manner in the m2-peptide/$gp120_{BaL}$ complex. The m2-peptide also "primes" gp120 to better expose the otherwise buried CD4 binding site, thereby enhancing its immunogenicity.

The present immunogens, particularly the m2-peptide/$gp120_{BaL}$ complex, elicit potent cross-reactive neutralizing antibodies in immunized recipients, specific for the CD4 binding site. Such antibodies are, by definition, highly preferred cross reactive neutralizing antibodies in that they target the most conserved functional-site of gp120, shared by all clades and isolates, and in doing so interfere directly with the ability of the virus to bind to its target cell. Prevention of attachment of HIV to CD4+ lymphocytes and macrophages is the most straightforward mechanism of neutralization. Thus, the response induced by the immunogenic compositions of the present invention that comprise the disclosed peptide/gp120 complexes is the desired goal of a prophylactic HIV/AIDS vaccine that can result in immunity, preferably antibodies, that effectively hinder the virus from binding to CD4 docking sites on target cells and prevent or slow viral infection.

In view of the foregoing, any means that enhance the immunogenicity of neutralizing epitopes of gp120 will be highly beneficial for producing a prophylactic AIDS immunogen and vaccine.

In one embodiment, the present invention is directed to a linear, single chain polypeptide (and a nucleic acid encoding it) that comprises a fusion between any of the peptides described, preferably m2, and an HIV-1 gp120 polypeptide, preferably gp120$_{BAL}$. The linkage is preferably via linker peptide. The peptide may be linked to the gp120 at either terminus. The linker must be long and flexible enough to allow this fusion product to fold naturally to manifest the CD4i structure due to the "internal" binding of the peptide to the gp120.

The invention also includes a nucleic acid molecule, preferably DNA, that encodes the above fusion polypeptide. Preferably, the nucleic acid comprises the peptide-coding sequence linked to a gp120 open reading frame, such that the polypeptide product is translated as a single polypeptide chain that natively folds to create the CD4i structure as noted above.

Amino Acid Substitution Variants

All amino acids listed above are L-amino acids unless it is specifically stated that they are D-amino acids. It should be understood that the present invention includes embodiments wherein one or more of the L-amino acids is replaced with its D isomer.

A preferred variant of the peptide of this invention is one in which a certain number of residues in the "invariant" positions of SEQ ID NO:1 or 2 are substituted conservatively with a different residue. For a detailed description of protein chemistry and structure, see Schulz, G. E. et al., *Principles of Protein Structure*, Springer-Verlag, New York, 1979, and Creighton, T. E., *Proteins: Structure and Molecular Principles*, W.H. Freeman & Co., San Francisco, 1984, which are hereby incorporated by reference.

Conservative substitutions are those that involve exchanges within one of the following groups:
  1. Small aliphatic, nonpolar or slightly polar residues e.g., Ala, Ser, Thr, Gly;
  2. Polar, negatively charged residues and their amides: e.g., Asp, Asn, Glu, Gln;
  3. Polar, positively charged residues: e.g., His, Arg, Lys;
  4. Large aliphatic, nonpolar residues: Met, Leu, Ile, Val (Cys); and
  5. Large aromatic residues: Phe, Tyr, Trp.

Tyr (in Group 5), because of its hydrogen bonding potential, has some kinship with Ser, Thr, etc. (Group 1). Pro, because of its unusual geometry, tightly constrains the chain.

Thus, the following substitutions in SEQ ID NO:1 (which are present also in SEQ ID NO:2 are intended:

| Substitutions | |
|---|---|
| Arg: | Lys or His, |
| Asp: | Asn, Glu, Gln |
| Leu: | Ile, Val, Met, Cys |
| Trp: | Phe, Tyr |
| Ala: | Gly, Ser, Thr, |

Certain commonly encountered amino acids which also provide useful substitutions include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,4-diaminobutyric acid (Dab); p-aminophenylalanine (Phe(pNH$_2$)); N-methyl valine (MeVal); homocysteine (hCys), homophenylalanine (hPhe) and homoserine (hSer); hydroxyproline (Hyp), homoproline (hPro), N-methylated amino acids (e.g., N-substituted glycine).

Covalent Modifications of Amino Acids and the Peptide

Covalent modifications of the peptide are included and may be introduced by reacting targeted amino acid residues of the peptide with an organic derivatizing agent that is capable of reacting with selected side chains or terminal residues.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5-7.0) which agent is relatively specific for the histidyl side chain. p-Bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents reverses the charge of the lysinyl residues. Other suitable reagents for derivatizing α-amino-containing residues include imidoesters such as methylpicolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high pK$_a$ of the guanidine functional group. Furthermore, these reagents may react with the groups of lysine as well as the arginine ε-amino group.

Modification of tyrosyl residues has permits introduction of spectral labels into a peptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups (aspartyl or glutamyl) are selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions. Either form of these residues falls within the scope of this invention.

Derivatization with bifunctional agents is useful for cross-linking the peptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azi-dosalicylic acid, homobifunctional imidoesters, including disuccinimidyl esters such as 3,3'-dithiobis(succinimidylpropionate), and bifunctional maleimides such as bis-N-maleimido-1,8-octane.

Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other chemical modifications include hydroxylation of proline and lysine, phosphorylation of the hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl.

Such chemically modified and derivatized moieties may improve the peptide's solubility, absorption, biological half life, and the like. These changes may eliminate or attenuate undesirable side effects of the proteins in vivo. Moieties capable of mediating such effects are disclosed, for example, in Gennaro, A R, *Remington: The Science and Practice of Pharmacy*, Lippincott Williams & Wilkins Publishers; 21st Ed, 2005 (or latest edition).

Production of m2 Synthetic Peptide and Its Use in the Formation of the m2-Peptide/gp120$_{BaL}$ Complex In one embodiment, synthetic peptides are used to formulate the peptide/gp120 complexes, preferably the m2/gp120$_{BaL}$ complexes. As described in the Examples, m1 peptide was produced as an MBP fusion protein, so that one is not limited to using the phage-derived peptide to work in this system (See Example 3 and FIG. 3).

Synthetic m2 peptide is commercially produced by solid phase chemical synthesis (for example by Biosight Ltd, Israel). Two different modes of cyclization can be employed (a) disulfide bonding between two Cys residues; and (b) covalent chemical bonding of side chains of Glu and Lys that would be introduced in place of the terminal Cys residues resulting in the peptide Glu-Asp-Arg-Arg-Asp-Leu-Pro-Asp-Trp-Ala-Ile-Arg-Ala-Lys (SEQ ID NO:19) or Lys-Asp-Arg-Arg-Asp-Leu-Pro-Asp-Trp-Ala-Ile-Arg-Ala-Glu (SEQ ID NO:20) in place of the m2 peptide Cys-Asp-Arg-Arg-Asp-Leu-Pro-Asp-Trp-Ala-Ile-Arg-Ala-Cys (SEQ ID NO:15).

Cyclization via flanking Glu and Lys residue side chains has an added advantage in that an N- or C-terminal Cys can be introduced to serve as a thiol donor for cross linking via a maleimide moiety.

The synthetic peptides can be made as monomers or conjugated to a branched poly-Lys or Lys dendrimers (4, 8 and 16 residues). Moreover, oligomers or multimers of any of the monomeric peptides of the present invention may be produced by conventional means, either as linear oligomers/multimers with or without linkers between the monomer repeats, or as tandem oligomers wherein the units are bonded by disulfide linkages or covalent bonds between Glu and Lys side chains as described above. Synthetic peptides are preferably purified at least to 80% purity by HPLC.

The peptides are examined for their ability (a) to bind efficiently to a selected gp120 (in the case of m2, to gp120$_{BaL}$) and (b) to induce CD4i conformation while (c) the gp120 molecule retains its CD4BS epitopes and CD4 binding site. Again, this is done by screening complexes against the panel of defining mAbs as in the study shown in FIG. 8.

For the phage-displayed peptides, the phage serves as a "scaffold" that is studded along its length with peptide- (e.g., m2-) bound gp120. This presentation is extremely efficient for immunogenic activity. Alternatively, synthetic peptides are efficiently expressed as N-terminal MBP fusions, so that synthetic m2 will also bind gp120$_{BaL}$ and induce the CD4i conformation without loss of the CD4BS epitopes.

The affinity of m2-peptide for gp120 may be sufficient for the complex to be administered as an immunogen without the need for cross linking Indeed the CG10 mAb was originally discovered by simply mixing gp120 with equimolar amounts of CD4, mixing the complex with adjuvant without cross linking, indicating that the complex was stable.

It is well-known that crosslinking can denature proteins. Nonetheless, crosslinkers are often used to stabilize immunogens or to inactivate pathogens that are used in vaccines. Therefore, use of crosslinkers is not incompatible with the present immunogens. Crosslinked immunogens are evaluated by testing the binding of the crosslinked complexes with a panel of defining mAb described herein using routine methods.

Immunogenicity Testing in Rabbits

Polyclonal antisera against, for example, m2/gp120$_{BaL}$ complexes are induced in rabbits. Preferably, female New Zealand White (NZW) rabbits about 3 months old from a commercial vendor are used. Each immunization group includes at least 4 rabbits.

Rabbits are immunized with complexes prepared as described and their sera obtained and tested for neutralizing activity. One reason for using rabbits is the large amounts of serum obtainable vs. smaller animals. Another reason for the preference is that rabbit Abs more closely resemble human antibodies (Abs) (than do mouse Abs) in that the CDR3 loops of the Ig heavy chains are longer. This characteristic has been proposed as being important for neutralizing Abs and particularly anti-HIV Abs (Collis, A V et al., 2003, *J Mol Biol* 325:337-54). The extended CDR3 loop is envisioned as being more likely to penetrate the narrow groove or cleft of the gp120 CD4 binding site.

Immunization of Rabbits:

Rabbits are preferably immunized s.c.+i.m., injecting a total volume 1 ml/animal. Examples are:

subcutaneous: 4 sites, 0.1 ml per site; (0.4 ml total)
intramuscular: 2 sites, 0.3 ml per site (0.6 ml total)

A preferred immunization and bleed schedule is shown in Table 2, below

TABLE 2

| Day | Week | Blood Draw | Immunize | ELISA | Neutralizing Ab Assay |
|---|---|---|---|---|---|
| −7 | −1 | Large Bleed (15-20 ml) | | (reserve preimmune) | |
| 0 | 0 | Large Bleed | Prime | X (preimmune) | X |
| 28 | 4 | | 1$^{st}$ Boost | | |
| 38 | | Small Bleed (5-10 ml) | | X | |
| 56 | 8 | | 2$^{nd}$ Boost | | |
| 66 | | Large Bleed | | X | X |
| 84 | 12 | | 3$^{rd}$ Boost | | |
| 94 | | Large bleed | | X | X |
| 112 | 16 | Exsanguination | | X | X |

Each rabbit receives 50 µg of complexed gp120$_{BaL}$ in each injection. When using phage displayed m2 peptide, 50 µg of gp120$_{BaL}$ is complexed with 2-3×10$^{12}$ phages per ml.

The antisera from these animals are tested for anti-gp120 activity by standard quantitative ELISA as used routinely in many laboratories, and antibody titers for each vaccine modality is determined, using gp120 or m2/gp120$_{BaL}$ complex as the antigen. In order to evaluate the immune response to the m2 component of the complex, phage displayed m2-peptide compared to vector-phage fth1 are used as an immobilized control antigen in the solid phase immunoassays.

To evaluate the potency of the serum and qualitative differences among different immunogens, it is useful to test whether anti-CD4 binding site antibodies are produced more efficiently in the complex-immunized animals compared to controls receiving gp120 alone. Because the CD4 binding site in the m2/gp120 complexes is accessible and possibly immunogenically enhanced, higher titers of anti-CD4 binding site antibodies are expected in the sera of the animals immunized with complexes vs. gp120 alone using routine competitive ELISA tests.

Briefly, gp120 is permitted to adsorb to the plate and serially diluted serum samples are added. After 1-2 hours incubation at room temperature, biotinylated CD4 is added to the wells and allowed to incubate for 1 hr. After washing, the wells are probed with streptavidin-HRP, washed and reacted with chromogenic substrate and the color reaction is measured. Controls include known anti-CD4 binding site antibodies, such as b12 mAb (Burton, D R et al., 1991, *Proc Natl Acad Sci USA* 88:10134-7).

m2 complexes of gp120 are at least as immunogenic as gp120 alone, so similar antibody titers are expected. Results can be normalized to the actual gp120 concentration administered per recipient irrespective of the m2 content in either of the two types of complex formulations. This permits comparison of the relative efficiencies of different the immunogen preparations in evoking the response.

Determining the Anti-HIV Neutralizing Activity of the Anti-m2/gp120 Sera.

Once serum samples have been evaluated for various binding activities, such as binding of gp120, the m2/gp120 complex, m2-peptide alone and specifically to the CD4 binding site of gp120, the sera are subjected to neutralization analyses, which includes the "three tier approach" to standardization of virus panels (Mascola, J R et al., 2005, *J Virol* 79:10103-7). Whereas serum binding to gp120 antigens may give a measure of the quantity of antibodies present as a measure of overall immunogenicity of a given antigen preparation, antibody titer alone does not necessarily correlate with neutralization activity on a given viral strain nor the extent of cross-reactive neutralization of a range of strains. Therefore an important consideration in establishing the value of a particular peptide/gp120 complex as a vaccine candidate is the ability to neutralize HIV-1 isolates representing at least a variety of Tier 2 viruses.

Neutralization is measured as a function of reduction in luciferase reporter gene expression after a single round of infection with molecularly cloned Env-pseudotyped strains of HIV-1 in TZM-b1 cells as described by Montefiori (Montefiori, D C, 2004, In *Current Protocols in Immunol*. Wiley & Sons). This assay has been optimized and formally validated. TZM-b1 cells are obtained from the NIH AIDS Research and Reference Reagent Program, as contributed by J. Kappes and X. Wu. This is a HeLa cell clone that was engineered to express CD4 and CCR5 (Platt, E J et al., 1998, *J Virol* 72:2855-64) and to contain integrated reporter genes for firefly luciferase and *E. coli* β-galactosidase under control of an HIV-1 LTR (Wei, X et al., 2002, *Antimicrob Agents Chemother* 46:1896-1905).

Briefly, 200 $TCID_{50}$ of Env-pseudovirus is incubated with a 1:10 dilution of serum sample in triplicate in a total volume of 150 μl for 1 hr at 37° C. in 96-well flat-bottom microplates. Freshly trypsinized cells ($10^4$ in 100 μl of growth medium containing 75 μg/ml DEAE dextran) are added to each well. Indinavir is added at a final concentration of 1 μM to prevent replication in the case of uncloned viruses. One set of control wells receives cells+virus (virus control) and another set receives cells only (background control). After 48 hr incubation, 100 μl of cells are transferred to 96-well black solid plates (Costar) for measurements of luminescence using Bright Glo® substrate solution as described by the supplier (Promega). Molecularly cloned Env-pseudoviruses are prepared by transfection in 293T cells. Cloned gp160s for pseudovirus production are derived from primary isolates.

Samples are assessed for magnitude and breadth of neutralization using a three tiered algorithm (Mascola et al., supra). Briefly, serum and plasma samples are first tested for the ability to neutralize the homologous vaccine strain(s) and one or more additional strains of virus that are highly sensitive to neutralization (Tier 1). Examples of Tier 1 viruses are the MN TCLA strain and the SF162 R5 strain, both of which are readily neutralized by multiple clades of HIV-1-positive serum samples and by sera from Env-immunized animals and humans. These Tier 1 assays detect any neutralizing antibodies that are present in the serum samples. Positive neutralization in Tier 1 assays justifies further testing to assess the extent of cross-neutralizing activity. For this, serum samples are tested in Tier 2 assays using primary isolate Env clones that are matched in genetic subtype to the vaccine strain(s). This Tier 2 analysis includes the standard panel of clade B HIV-1 reference strains (Li, M et al., 2005, *J Virol* 79:10108-

25). Positive neutralization in Tier 2 assays justifies a final round of testing in Tier 3 assays using primary isolate Env clones from other genetic subtypes. This three-tiered algorithm minimizes the number of assays to be performed in cases of weak immunogens and enables acquisition of large data sets for enhanced statistical power in cases of stronger immunogenicity.

A preferred and most valuable immunogenic peptide/gp120 complex is one that elicits potent cross-reactive neutralizing activity against HIV primary isolates. The use of $gp120_{BaL}$ permits comparison of the performance of, e.g., m2/$gp120_{BaL}$ with results of studies that used this same strain and tested cross linked CD4/gp120 has as well as the A32 studies described by Liao et al., supra.

Adjuvants, Immune Stimulants and Immunogen Formulations

The immunogenicity of the present immunogen is enhanced in the presence of exogenous adjuvants, immune stimulants, depot materials, etc. Thus in addition to the peptide/gp120 immunogenic complex described herein, the present immunogenic composition preferably includes one or more adjuvants or immunostimulating agents.

Examples of adjuvants or agents that may add to the effectiveness of the protein immunogen as an immunogen include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives (such as QS21®), liposomes, levamisole, DEAE-dextran, blocked copolymers or other synthetic adjuvants. Another adjuvant is ISAF-1 (5% squalene, 2.5% pluronic L121, 0.2% Tween 80 in phosphate-buffered solution with 0.4 mg of threonyl-muramyl dipeptide (Kwak, L W et al., 1992, *N. Engl. J. Med.,* 327: 1209-1238). Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen® (oil-in-water), Alhydrogel® (aluminum hydroxide), or a mixture of Amphigen® and Alhydrogel®. Aluminum is approved for human use. The vaccine material may be adsorbed to or conjugated to beads such as latex or gold beads, ISCOMs, and the like. General methods to prepare vaccines are described in *Remington's Pharmaceutical Sciences*, Gennaro, supra).

The adjuvant is preferably one or more of (a) Ribi adjuvant (b) ISAF-1 (5% squalene, 2.5% pluronic L121, 0.2% Tween 80) in phosphate-buffered solution with 0.4 mg of threonyl-muramyl dipeptide; (c) Amphigen®; (d) Alhydrogel®; (e) a mixture of Amphigen® and Alhydrogel® (f) QS21®; or (G) monophosphoryl lipid A adjuvant. A preferred adjuvant is monophosphoryl lipid.

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Adjuvants, including liposomes, are discussed in the following references, incorporated herein by reference: Gregoriades, G. et al., *Immunological Adjuvants and Vaccines*, Plenum Press, New York, 1989; Michalek, S. M. et al., 1989, *Curr. Top. Microbiol. Immunol.* 146:51-8.

Additional discussion of vaccine design, particularly controlled release systems, can be found in Powell, M. F. et al. (eds), *Vaccine Design: The Subunit and Adjuvant Approach*, Powell, M. F. et al. (eds), Plenum Press, New York, 1995, p 389-412. Controlled release systems are already used in humans as "depots" to deliver drugs and hormones (Langer, R., 1990, *Science* 249: 1527-1533). Such systems may have a significant impact on immunization as they can be designed to deliver controlled amounts of the immunogen continuously or in spaced pulses at predetermined rates (Cohen et al., 1991, *Pharm. Res.* 8:713-720; Eldridge et al., 1991a, *Mol. Immunol.* 28:287-294; Gander et al. 1993, in: *Proc. Int. Syn. Control. Rel. Bioact. Mater*., Controlled Release Society, Washington, D.C., pp. 65-66), while simultaneously protecting undelivered antigenic material from rapid degradation in vivo. Controlled release microspheres have considerable potential for oral immunization (Edelman et al., 1993, *Vaccine* 11:155-158; Eldridge et al., 1990, *J. Control. Rel.* 11:205-214; McQueen et al., 1993, *Vaccine* 11:201-206; Moldoveanu et al., 1989, *Curr Top. Microbiol. Immunol.* 146:91-99; O'Hagan et al., 1993b, *Vaccine* 11: 149-154; Reid et al. 1993, *Vaccine* 11:159-167). Other potential advantages of polymeric controlled release systems include: lower dosage requirements leading to decreased cost; localized or targeted delivery of antigen to antigen-presenting cells or the lymphatic system; more than one antigen may be encapsulated, facilitating the design of a formulation that can immunize an individual against more than one protein or against several epitopes in a single injection; and improved patient compliance. In addition, controlled release systems may reduce the number of immunogen doses required for optimal vaccination to a single injection.

Microspheres are particularly suited as controlled release immunogen carriers for two reasons: (1) particles greater than 10 μm in diameter are capable of providing a long-term persistence of antigen at the site of injection which may be necessary for a sustained high-level antibody immune response and (2) microparticles in the size range of 1-10 μm are readily phagocytosed by macrophages (Eldridge et al., 1989, *Adv. Exp. Med. Biol.* 251:192-202; Tabata et al., 1988, *Biomaterials* 9:356-362; *J. Biomed Mater Res.* 22:837-858) leading to direct intracellular delivery of antigen to antigen-presenting cells.

Microsphere phagocytosis by macrophages may be increased by altering the surface characteristics, as microspheres with hydrophobic surfaces are generally more readily phagocytosed than those with hydrophilic surfaces (Tabata et al., 1988, *Biomaterials* 9:356-362; Tabata et al., 1990, *Crit. Rev. Ther Drug Carrier Syst.* 7:121-148).

Among the advantages of using polymer microspheres for immunogen delivery is the ability to control the time following administration at which the antigen is released. This capability allows the fabrication of a single-injection formulation that releases multiple "pulses" of the immunogen or immunogen at predetermined times following administration (Gilley et al., 1992, In: *Proc. Int. Symp. Control. Rel. Bioact. Mater*, Controlled Release Society, Orlando, pp. 110-111). Antigen release kinetics from polymer microspheres can be controlled to a great extent by the simple manipulation of such variables as polymer composition and molecular weight, the weight ratio of immunogen to polymer (i.e., the immunogen loading), and microsphere size (Hanes et al., In: *Reproductive Immunology*, 1995, R. Bronson et al., eds, Blackwell. Oxford).

Formulations that contain a combination of both small (1-10 μm) and larger (20-50 μm) microspheres may produce higher and longer-lasting responses compared to the administration of immunogen encapsulated in microspheres with diameters of exclusively 1-10 or 20-50 μm (Eldridge et al., 1991a, *Mol. Immunol.* 28287-294). In one study, tetanus toxoid (TT)-containing microspheres were tailored to produce a strong priming antigen dose released over the first few days after injection followed by two "boosting" doses released after 1 and 3 months, respectively, in order to mimic conventional vaccination schedules (Gander et al., supra).

The most widely used polymers for vaccine microencapsulation have been the polyesters based on lactic and glycolic acid. These polymers have several advantages, including extensive data on their in vitro and in vivo degradation rates (Lewis, 1990, In: *Biodegradable Polymers as Drug Delivery Systems* (Chasin and Langer, eds.), Dekker, New York, pp. 1-41; Tice and Tabibi, 1992, In: *Treatise on Controlled Drug Delivery* (A. Kydonieus, ed.), Dekker, New York, pp. 315-39, and FDA approval for a number of clinical applications in humans such as surgical sutures (Gilding et al., 1979, *Polymer* 20:1459-1464; Schneider, 1972, U.S. Pat. No. 3,636,956) and a 30-day microsphere-based controlled delivery system for leuprolide acetate (Lupron Depot) (Okada et al., 1991, *Pharm. Res.* 8:787-791).

Several alternatives to the lactide/glycolide polyesters include biodegradable polymers that degrade to give molecules with adjuvant properties, and may prove particularly useful as carriers of more weakly immunogenic antigens. Because of the know adjuvanticity of L-tyrosine derivatives (Wheeler et al, 1982, *Int. Arch. Allergy Appl. Immunol.* 69:113-119; Wheeler et al., 1984, *Int. Arch. Allergy Appl. Immunol.* 75:294-299), a polymer based on a dityrosine derivative was synthesized by Langer and colleagues (Kohn et al., 1986, *Biomaterials* 7:176-82) and studied using as a model antigen bovine serum albumin, BSA (Kohn et al., 1986, *J. Immunol. Methods* 95:31-38). Biodegradable poly (CTTH iminocarbonate) was selected since its primary degradation product N-benzyloxycarbonyl-L-tyrosyl-L-tyrosine hexyl ester (CTTH), was found to be as potent an adjuvant as complete Freund's (CFA) and muramyl dipeptide (MDP).

Because of its inherent propensity to be phagocytosed by macrophages (Tabata et al., 1986, *J. Bioact. Compat. Polym.* 1:32-46) and its extensive use in pharmaceutical and medical applications, gelatin is a useful polymer for vaccine microencapsulation (Tabata et al., 1993, in: *Proc. Int. Symp. Control. Rel. Bioact. Mater*, Controlled Release Society, Washington, D.C., pp. 392-393). Gelatin microspheres have also been used to encapsulate immunostimulators, such as MDP and interferon-α (Tabata et al., 1987, *J Pharm Pharmaco.* 39:698-704; 1989b, *Pharm. Res.* 6:422-427). Microsphere-encapsulated MDP activates macrophages in much shorter periods than free MDP at concentrations approximately 2000 times lower. A combination of MDP and vaccine-containing gelatin microspheres may yield a very potent vaccine formulation.

Liposomes are often unstable in vivo, most likely because of their rapid destruction by macrophages and high-density lipoproteins (Schreier et al., 1987, *J. Control. Rel.* 5: 187-192), and therefore provide only a brief antigen depot effect when injected subcutaneously or intramuscularly (Eppstein et al., 1985, *Proc. Natl. Acad Sci. USA* 82:3688-3692; Weiner et al., 1985, *J. Pharm. Sci.* 74:922-925). One approach to extending the in vivo lifetime of liposomes (Cohen et al., 1991, *Proc. Natl. Acad. Sci. USA* 88:10440-10444) is use of alginate polymers to encapsulate immunogen-containing liposomes into microspheres, thereby protecting them from rapid destruction in vivo. Enzymatically activated microencapsulated liposomes (MELs) that are capable of providing pulsatile immunogen release kinetics have also been prepared (Kibat et al., 1990, *FASEB J.* 4:2533-2539). MELs are also expected to show increased stability as a carrier for oral administration.

A variety of methods may be used to prepare immunogen-loaded polymer microspheres that are capable of a wide range of release patterns and durations. The method of choice usually is determined by the relative compatibility of the process conditions with the antigen (e.g., the method that results in the least loss of immunogenicity) and the polymer excipient used, combined with the ability of the method to produce appropriately sized microspheres.

Solvent evaporation techniques are popular because of their relative ease of preparation, amenability to scale-up, and because high encapsulation efficiencies can be attained. Of particular importance for immunogens that are sensitive to organic solvents may be the multiple emulsion technique (Cohen et al., 1991, *Pharm. Res.*, supra). Spray drying and film casing techniques have also been used to prepare monolithic polymer microspheres.

Microcapsules consist of an immunogen-loaded core surrounded by a thin polymer membrane and, as a result, are often referred to as "reservoir" systems.

Carrier and immunogen stability during device development, storage, and in vivo depoting are a matter for concern. Polypeptide antigens may have fragile three-dimensional structures that are vital to immunogenicity. This three-dimensional structure may be compromised or lost as the antigen denatures or aggregates. Exposure to organic solvents, rehydration after lyophilization on exposure to moisture, or complex chemical interactions with the polymer excipient or other chemicals in the preparation of a controlled release device may result in loss or reduction of immunogenicity of protein-based vaccines. The following documents describe stabilization of complex antigens (Arakawa et al., 1993, *Adv. Drug Deliv. Rev.* 10: 1-28; Liu et al., 1991, *Biotechnol. Bioeng.* 37:177-184; Volin and Klibanov, 1989, In: *Protein Function: A Practical Approach* (T. E. Creighton, ed.). IRL Press, Oxford, pp. 1-24).

An advantage of polymer microsphere formulations is that many polymers are stable at room temperature for extended periods of time if kept dry. For example, lactide/glycolide polyesters have been reported to be stable if kept dry and below about 40° C. (Aguado et al., 1992, *Immunobiology* 184:113-125). In addition, vaccine can be stored in the dry state within microsphere formulations, an important advantage considering susceptibility of some proteins to moisture-induced aggregation (Liu et al., supra).

The compositions preferably contain (1) an effective amount of the immunogenic complex together with (2) a suitable amount of a carrier molecule or, optionally a carrier vehicle, and, if desired, (3) preservatives, buffers, and the like. Descriptions of formulations are found in Voller, A. et al., *New Trends and Developments in Vaccines*, University Park Press, Baltimore, Md., 1978).

In one embodiment, the immunogenic composition includes one or more cytokines such as IL-2, GM-CSF, IL-4 and the like. Proinflammatory chemokines may be added, e.g., interferon inducible protein 10 and MCP-3 (Biragyn A et al., 1999, *Nature Biotechnol.* 17:253-8). In general, it appears that any cytokine or chemokine that induces or promotes inflammatory responses, recruits antigen presenting cells (APC) and promotes targeting of APC for chemokine receptor-mediated uptake of the polypeptide antigen is useful in the present formulation.

As with all immunogenic compositions for eliciting immunity, the immunogenically effective amounts of the polypeptide complex of the invention must be determined empirically. Factors to be considered include the immunogenicity of the present peptide/gp120 complexes is whether or there will occur further complexing with, or covalent bonding to, an adjuvant or carrier protein or other carrier and the route of administration and the number of immunizing doses to be administered. Such factors are known in the vaccine art, and it is well within the skill of immunologists to make such determinations without undue experimentation.

The proportion of the protein immunogen and the adjuvant can be varied over a broad range so long as both are present in effective amounts. For example, aluminum hydroxide can be present in an amount of about 0.5% of the mixture ($Al_2O_3$ basis).

After formulation, the composition may be incorporated into a sterile container which is sealed and stored at low temperatures., for example 4° C. or −20° C. or −80° C. Alternatively, the material may be lyophilized which permits longer-term storage in a stabilized form.

The pharmaceutical preparations are made following conventional techniques of pharmaceutical chemistry. The pharmaceutical compositions may also contain minor amounts of nontoxic auxiliary substances such as wetting or emulsifying agents, pH buffering agents and so forth. The peptides/complexes are formulated using conventional pharmaceutically acceptable parenteral vehicles for administration by injection. These vehicles are nontoxic and therapeutic, and a number of formulations are set forth in *Remington's Pharmaceutical Sciences*, supra. Nonlimiting examples of excipients are water, saline, Ringer's solution, dextrose solution and Hank's balanced salt solution. Formulations according to the invention may also contain minor amounts of additives such as substances that maintain isotonicity, physiological pH, and stability. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension. Optionally, a suspension may contain stabilizers.

The peptides and other useful compositions of the invention are preferably formulated in purified form substantially free of aggregates and other protein materials, preferably at concentrations of about 1.0 ng/ml to 100 mg/ml.

Virus, Bacteriophage or Bacteria as Immunogenic Carrier

In a further variation, the immunogenic peptide or complex of the present invention, can be presented by a virus or a bacterium as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus and other rhabdo viruses, vaccinia and fowl pox. Suitable bacteria include *Salmonella* and *Shigella*.

The display of short peptides such as those that comprise immunogenic epitopes fused to a phage surface also serve as a useful immunogen. Filamentous bacteriophages are excellent vehicles for the expression and presentation of foreign peptides in a variety of biological systems (Willis, E A et al., 1993, *Gene* 128:79-83; Meola, A et al., 1995, *J. Immunol.* 154: 3162-72: Bastein, N et al., 1997, *Virology* 234:118-22). Administration of filamentous phages induces a strong immune response to the phage proteins in all animals tested, without any evidence of toxic effects. Phage proteins pIII and pVIII are proteins that have been often used for phage display. Furthermore, recombinant filamentous phage are used to produce a source of specific peptides, e.g., for use as antigens. An important advantage of this approach over chemical synthesis is the fact that the products obtained are the result of the biological fidelity of translational machinery and are not subject to the 70-94% purity levels common in the solid-phase synthesis of peptides. The phage presents an easily renewable source of the peptide, as additional material can be produced by growth of bacterial cultures. Genetically engineered filamentous phages thus serve as a means of obtaining both the peptide and an immunogenic carrier for antibody production without necessitating the use of an adjuvant. See, also, Frenkel, D et al., 2000, *Proc Natl Acad Sci USA* 97: 11455-59)

Immunization with phage displayed peptides typically requires $10^{10}$ to $10^{12}$ phage particles per injection. A method such as that described by Yip, Y L et al., 2001, *Immunol Lett* 79:197-202) may be used. This method employs $10^{12}$ phages/100 µl for ip immunization of mice; similar phage doses are appropriate for immunization of rabbits.

Production of phages in *E. coli* cells routinely generates $10^{13}$ phages per 0.5-1.0 liters of culture medium. Production of adequate amounts of phage displayed m2-peptide for the intended pilot study is therefore straightforward. $gp120_{BaL}$ is commercially available, and gp120 or gp160 expression vectors and vaccinia expression vectors of BaL strain molecule are readily available.

Peptides can be displayed on filamentous phages on either the pIII protein (five copies per phage) or, on the pVIII protein (2700 copies per phage) (Yip et al., supra). The fth1 expression system displays peptides on pVIII protein in chimeric phages where recombinant pVIII proteins are incorporated in a majority of wild-type pVIII proteins, thereby generating a mosaic phage. Assuming only 200 m2 peptides per phage (i.e., less than 10% recombinant pVIII proteins), one can bind 20 µg of gp120 to $10^{12}$ phages used for immunization.

In order to ascertain that the bound gp120 is in the correct CD4i conformation, binding of the 17b or CG10 mAbs is monitored. Preparations of a peptide/gp120 complex, exemplified here by the m2/gp120$_{BaL}$ complex, are tested against the panel of the seven defining mAbs as well as CD4. To ensure the complexed nature of gp120 throughout immunization process, routine chemical cross-linking can be employed (e.g., DeVico et al., 1995, supra; Fouts et al., 2000, supra).

If desired a variety of cross linkers can be screened to ensure that a compatible cross-linker is found that stabilizes the m2-peptide/gp120 complex without hindering the antigenicity of the CD4i and CD4BS epitopes or the CD4 binding site. For this, the m2-peptide/$gp120_{BaL}$ complex is prepared in a Tris buffer, a phosphate buffer, or any other standard, compatible buffer, and reacted with various homobifunctional and heterobifunctional cross linking agents overnight on ice. The m2 sequence Cys-Asp-Arg-Arg-Asp-Leu-Pro-Asp-Trp-Ala-Ile-Arg-Ala-Cys (SEQ ID NO:15) contains 6 potential functional R groups for cross linking (underscored). The abundance of free carboxyl groups should allows the use of carbodiimide-based cross linkers. Also the three Arg residues lend themselves cross-linkers such as p-azidophenyl glyoxal monohydrate (APG; Pierce Biotechnology Inc).

The second functional active group depends on the location at which m2 binds to gp120. Thus for example, since gp120 is highly glycosylated, hydrazido heterobifunctional cross linkers may be particularly efficient, locking m2 in position without impacting the amino acids of gp120. For this, gp120 will first be treated with periodate to generate the required aldehyde moieties from the vicinal sugar hydroxyls. Generally, it is preferred that cross-linkers be determined empirically using ordinary skill in the art.

There is little need to further purify the complex given that CsCl gradient-purified phage displayed m2-peptides or synthetic peptides are used along with pure (commercial) gp120. Alternatively, a CD4− or mAb affinity column (using for example 17b or CG10) can be employed to purify functional complexes from monomers or non-functional complexes as well as unreacted cross linkers. In one embodiment, the verified functional phage displayed m2-peptide/$gp120_{BaL}$ complex is used as the test immunogen.

Other examples of useful bacteriophage vectors are Fuse 5 and f88, as well as phage-peptide libraries based on peptides of, for example 8-20 amino acids as disclosed herein.

A library sample containing $10^9$ phage particles is subjected to three rounds of biopanning and amplification. See, for example, Frenkel, D et al., 1999, *J. Neuroimmunol.* 95:136-42. The selected phages are tested for their ability to bind to an anti-phage antibody by ELISA assays. Wells of microplates are coated with appropriate dilutions of an anti-antibody preparation, for example, rabbit anti-phage anti serum, and incubated overnight at 4° C. Positive phage clones are propagated, and their DNA is sequenced in the insert region.

Recombinant phage displaying the peptide of choice as fusion of protein VIII, are selected and produced in large quantities for immunization. For example a 2-ml overnight culture of a colony of an appropriate *E. coli* strain or mutant is grown at 37° C. in 2YT medium, for example, containing tetracycline. An aliquot of this preculture is used to subculture 1 liter of 2YT/tet containing 2 mM isopropyl-D-thiogalactoside. After 16 h of incubation at 37° C., the culture is centrifuged at 7,500×g for 30 min, and the supernatant with infectious phages is precipitated at 4° C. for 2 h by the addition of 0.15 volume of a solution containing polyethylene glycol-8000 and concentrated NaCl. After centrifugation, the phage pellet is resuspended in PBS and centrifuged again for bacteria contamination release; the supernatant is re-precipitated and resuspended in PBS and the phage concentration is estimated spectrophotometrically (1 OD unit at 269 nm represents $10^{11}$ phage/ml).

A phage preparation is preferably inactivated by UV before use in immunization, for example, as in Galfre, G et al., 1997, *Vaccine* 15:1276-85.

Dendritic Polymers/Dendrimers.

This embodiment is based on the knowledge in the art that a multiple antigen peptide carrying a multiplicity of epitopes induces superior immune responses compared to responses following immunization with corresponding equal amounts of monovalent epitopes The present invention is intended to broadly encompass antigenic products carrying multiple copies of the peptides of the present invention an in a multiple antigen peptide system.

The present dendritic polymers are antigenic product according to the present based on dendritic polymer in which an antigens/epitope or epitopes are covalently bound to the branches that radiate from a core molecule. These dendritic polymers are characterized by higher concentrations of functional groups per unit of molecular volume than ordinary polymers. Generally, they are based upon two or more identical branches originating from a core molecule having at least two functional groups. Such polymers have been described by Denkewalter et al. in U.S. Pat. No. 4,289,872 and by Tomalia et al. (U.S. Pat. Nos. 4,599,400 and 4,507,466). Other polymers of this class were described by Erickson in U.S. Pat. No. 4,515,920. See, also, Solomon, US Patent Publication 20050053575.

The polymers are often referred to as dendritic polymers because their structure may be symbolized as a tree with a core trunk and several branches. Unlike a tree, however, the branches in dendritic polymers are substantially identical.

This dendrite system has been termed the "multiple antigen peptide system" (MAPS), which is the commonly used name for a combination antigen/antigen carrier that is composed of two or more, usually identical, antigenic molecules covalently attached to a dendritic core which is composed of principal units which are at least bifunctional/difunctional. Each bifunctional unit in a branch provides a base for added growth.

The dendritic core of a multiple antigen peptide system can be composed of lysine molecules. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen (MAP). The process can be repeated to form fourth or even higher generations of molecules. With each generation, the number of free amino groups increases geometrically and can be represented by 2.sup.n, where n is the number of the generation. Alternatively, the second generation molecule having four free amino groups can be used to form a tetravalent MAP with four peptides covalently linked to the core. Many other molecules, including, e.g., the amino acids Asp and Glu, both of which have two carboxyl groups and one amino group to produce polyAsp or polyGlu with $2_n$ free carboxyl groups, can be used to form the dendritic core of MAPS.

The term "dendritic polymer" is sometimes used herein to define a product of the invention. The term includes carrier molecules which are sufficiently large to be regarded as polymers as well as those which may contain as few as three monomers.

The chemistry for synthesizing dendritic polymers is known and available. With amino acids, the chemistry for blocking functional groups which should not react and then removing the blocking groups when it is desired that the functional groups should react has been described in detail in numerous patents and scientific publications. The dendritic polymers and the entire MAP can be produced on a resin as in Merrifield synthesis and then removed from the polymer. Tomalia utilized ammonia or ethylenediamine as the core molecule. In this procedure, the core molecule is reacted with an acrylate ester by Michael addition and the ester groups removed by hydrolysis. The resulting first generation molecules contain three free carboxyl groups in the case of ammonia and four free carboxyl groups when ethylenediamine is employed. Tomalia and colleagues (see below) extended the dendritic polymer with ethylenediamine followed by another acrylic ester monomer, and repeats the sequence until the desired molecular weight was attained. It is readily apparent to one skilled in the art, that each branch of the dendritic polymer can be lengthened by any of a number of selected procedures. For example, each branch can be extended by multiple reactions with Lys molecules.

Erickson (supra) utilized the classic Merrifield technique in which a polypeptide of substantially any desired molecular weight is grown from a solid resin support. As the technique is utilized for the preparation of dendritic polymers, the linking molecule which joins the polymer to the resin support is trifunctional. One of the functional groups is involved in the linkage to the resin, the other two functional groups serve as the starting point for the growth of the polymer. The polymer is removed from the resin when the desired molecular weight has been obtained. One standard cleavage procedure is treatment with liquid hydrogen fluoride at 0° C. for one hour. Another, and more satisfactory procedure, is to utilize a complex of hydrogen fluoride and dimethylsulfide (HF:DMF) as described (Tam et al., 1983, *J Amer Chem Soc* 105:6442) to minimize side reactions and loss of peptide.

In one example, Denkewalter et al. (supra) utilized Lys as the core molecule. The amino groups of the core molecule are blocked by conversion to urethane groups. The carboxyl group is blocked by reaction with benzhydrylamine. Hydrolysis of the urethane groups generates a benzhydrylamide of lysine with two free amino groups which serve as the starting points for the growth of the dendritic polymer.

This brief discussion of three of the available procedures for producing dendritic polymers should be adequate those skilled in the art to depart from these general teachings and teaches the skilled artisan the salient features of the polymers, such as the provision of a large number of available functional groups in a small molecular volume. The result is that a high concentration of epitopes in a small volume can be attained by joining the epitopes/antigen to those available functional groups. The resulting product contains a high proportion of the epitopes on a relatively small carrier, (the antigen:carrier ratio is quite high). This contrasts with other, conventional products used for formulating vaccines which typically comprise a small amount of antigen on a large amount of carrier.

Other important features of the dendritic polymer as an immunogenic carrier are that the precise structure is known; there are no "antigenic" contaminants or those that irritate tissue or provoke other undesirable reactions. The precise concentration of the peptide or peptide/gp120 complex is known; and is symmetrically distributed on the carrier; and the carrier can be utilized as a base for more than one peptide or complex so that multivalent immunogens or vaccines can be produced.

When the MAPS is to be employed to produce a vaccine or immunogenic composition, it is preferred that the core molecule of the dendrimer be a naturally occurring amino acid such as Lys so that it can be properly metabolized. However, non-natural amino acids, even if not a-amino acids, can be employed. The amino acids used in building the core molecule can be in either the D or L-form.

More details about the chemistry and pharmaceutical use of dendritic polymers can be found in Tomalia D A et al., 2007, *Biochem Soc Trans*. 35:61-7; Braun C S et al., 2005, *J Pharm Sci*. 94:423-36; Svenson S et al., 2005, *Adv Drug Deliv Rev*. 57:2106-29 and the following U.S. Pat. Nos. 4,289, 872; 4,558,120; 4,376,861; 4,568,737; 4,507,466; 4,587,329; 4,515,920; 4,599,400; 4,517,122; and 4,600,535.

A resin-bound dendritic polymer can be employed in the practice of this invention. Such preparations may be obtained commercially from a number of suppliers (e.g., Advanced ChemTech, Inc. Louisville, Ky.). The polymer may be cleaved from the resin using HF:DMS as a preferred agent. The dendritic polyLys built from a Gly linker originally joined through a benzyl linker to the resin. Other linkers such as Ala can be employed or the linker may be omitted, or linker molecules can be utilized.

Doses and Routes of Immunization

A preferred effective dose for treating a subject in need of the present treatment, preferably a human, is an amount of up to about 100 milligrams of active compound per kilogram of body weight. A typical single dosage of the peptide/gp120 complex is between about 1 μg and about 100 mg/kg body weight, and preferably from about 10 μg to about 50 mg/kg body weight. A total daily dosage in the range of about 0.1 milligrams to about 7 grams is preferred for intramuscular (i.m.) or s.c. administration.

The foregoing ranges are, however, suggestive, as the number of variables in an individual treatment regime is large, and considerable excursions from these preferred values are expected. As is evident to those skilled in the art, the dosage of an immunogenic composition may be higher than the dosage of the compound used to treat infection (i.e., limit viral spread). Not only the effective dose but also the effective frequency of administration is determined by the intended use, and can be established by those of skill without undue experimentation. The total dose required for each treatment may be administered by multiple doses or in a single dose. The peptide complex may be administered alone or in conjunction with other therapeutics directed to the treatment of the disease or condition.

Pharmaceutically acceptable acid addition salts of certain compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

The compounds of the invention, as well as the pharmaceutically acceptable salts thereof, may be incorporated into convenient dosage forms, such as capsules, impregnated wafers, tablets or preferably injectable preparations. Solid or liquid pharmaceutically acceptable carriers may be employed.

Preferably, the compounds of the invention are administered systemically, e.g., by injection or infusion. Administration may be by any known route, preferably intravenous, subcutaneous, intramuscular or intraperitoneal. Other acceptable routes include intranasal, intradermal, intrathecal (into an organ sheath), etc.

Having now generally described the invention, the same will be more readily understood through reference to the following examples which are provided by way of illustration, and are not intended to be limiting of the present invention, unless specified.

EXAMPLE 1

Binding of m1 Peptide (SEQ ID NO:3) to gp120 Elicits CD4i Conformation

The native conformation of gp120 has evolved and been selected to evade immune defenses. However, gp120 is highly flexible and constantly flutters through a variety of conformations, some of which may be more or less stable, that are able to transiently display epitopes that could effectively elicit neutralizing antibodies (Pantophlet et al., 2006, supra). Binding of CD4 to gp120 locks gp120 into a unique conformation that displays novel CD4i epitopes. It has been proposed that other conformations of gp120 may exist, some of which may be intermediate between the native conformation and that induced by CD4 binding (Pan) et al., 2005, supra).

The present inventors began to isolate gp120-binding peptides that would be used as immunomodulators. Earlier studies by others (Liao et al., supra; Manoutcharian, K et al., 2004, *Vet Immunol Immunopathol* 99:11-24) used random peptide libraries to identify lead peptides as potential inhibitors of infection. Thus screening of combinatorial phage display libraries of random peptides led to the affinity selection of a number of gp120 binders a few of which indeed compete for CD4 binding while others enhance to some degree binding of mAb 17b (Liao et al., supra).

Another example of a search for inhibitory peptides (Choi, Y H et al, 2001, *J Med Chem* 44, 1356-63) showed that specific peptides designed to simulate Phe43 of CD4 can be isolated and can inhibit the CD4-gp120 interactions.

The present invention differs from the foregoing approaches in that is focuses on binding of specific peptides to gp120 that lock the envelope in a preferred conformation, restricting its flexibility and stabilizing it as an improved immunogen.

In initial studies, soluble monomeric gp120$_{451}$ was used to screen a phage display library in which random 12mer peptides flanked by constant cysteine residues were fused to the N terminus of fd-phage protein 8 (Enshell-Seijffers, D et al., 2001, *Nucleic Acids Res* 29, E50-0; Enshell-Seijffers, D et al., 2002, In: *Curr Protocols Immunol* (Coico, R., ed.), Vol. 2, pp. 9.8.1-9.8.27. John Wiley and Sons). Consecutive biopanning of the library against immobilized gp120 led to a progressive increase in the number of phages eluted in each cycle. After amplification of the eluted phages, an ever increasing capacity to specifically bind gp120 was found.

Of the gp120-binding peptides isolated, one was particularly unique. As illustrated in FIG. 1, phages that display the m1-peptide, specifically bind gp120 and in doing so elicit the CG10 epitope. As noted above, binding of CG10 to its epitope is absolutely dependent on the CD4i conformation of gp120. It was concluded that m1 binds to the CD4 binding site and acts as a CD4 mimetic, triggering a structural rearrangement locking gp120 into the CD4i conformation.

EXAMPLE 2 m1 Peptide does not Occlude CD4 Binding Site on gp120

Figure 2:
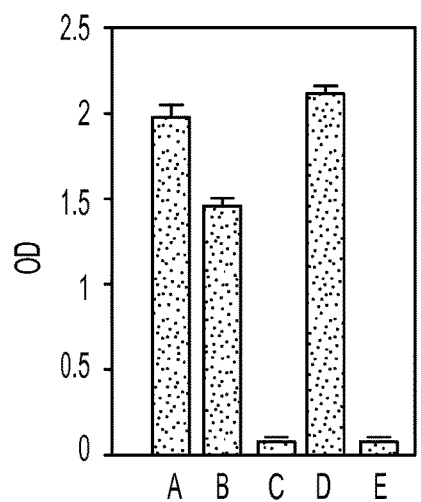
FIG. 2A-2E show that CD4 enhances m1 binding to gp120. Anti-M13 (phage) antibody was adsorbed to microplate wells to capture either m1 peptide-expressing phages (A, B, D, E) or fth1-negative control phage (C). Then gp120/CD4 complex (A, C, D), gp120 (B) or CD4 (E) were incubated with the captured phages and probed with anti-gp120 mAb (A-C) or anti CD4 mAb (D, E). Note, CD4 does not bind m1 (E), does not inhibit m1 binding to gp120 (A and D) and markedly enhances gp120 binding by m1 (compare with B).

Surprisingly, it was discovered that m1 is not a CD4 mimetic and does not occlude the CD4 binding site. As demonstrated by the results in FIG. 2 the m1-peptide binding to gp120 (B) is not inhibited, as one might expect, when gp120 is complexed with CD4, but markedly enhanced instead (A and D). Note, m1 has no affinity for CD4 alone (E).

EXAMPLE 3

A Fusion Peptide Comprising m1 Binds gp120

Figure 3:
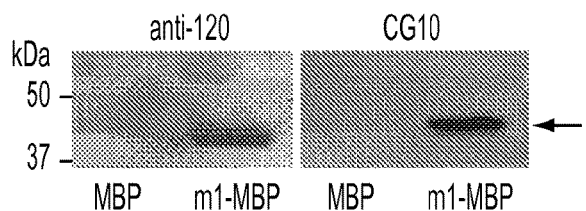
FIG. 3 shows that fusions of m1 peptide to maltose binding protein (MBP) bind gp120 and induce the CG10 epitope. Oligonucleotides corresponding to m1 peptide were introduced at the 5' end of MBP DNA to create an N-terminal fusion of m1 to MBP. E. coli transformed with this expression-vector with m1 peptide (m1-MBP) or without m1 peptide (MBP) were induced for expression and osmotically lysed. Proteins in the lysate were resolved by SDS-PAGE and blotted onto nitrocellulose membrane filters. The blots were then incubated with gp120 to evaluate the ability of the resolved MBP proteins to bind gp120. Blots were further probed with either anti-gp120 mAb or CG10. The arrow indicates the position of m1-MBP fusion protein.

When expressed as a peptide in a fusion protein (i.e., outside the context of a phage library), m1 continued to bind gp120 and induce the CG10 epitope. FIG. 3 shows that a fusion of maltose binding protein (MBP) with m1 at its N terminus binds gp120 and continues to induce the CG10 epitope. This result illustrates that m1-peptide does not require phage-derived amino acids for its activity and can function outside the context of the phage display system. It was concluded that a functional synthetic-peptide version of the m1-peptide (or its derivative m2-peptide) has the same activity.

EXAMPLE 4

Figure 4:
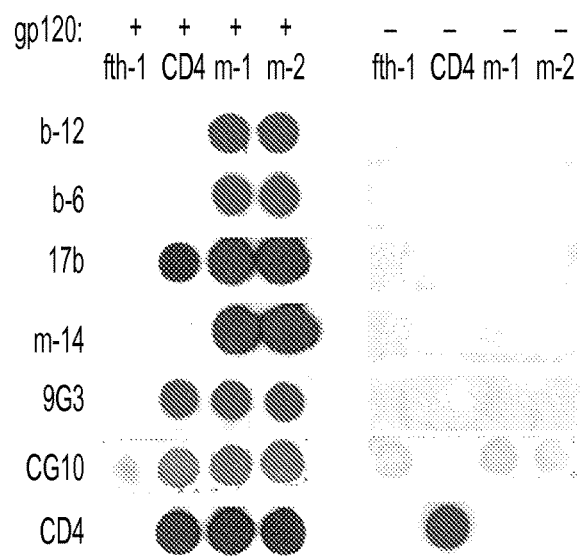
FIG. 4 is a dot blot analysis of binding of "defining" mAbs to gp120$_{451}$ complexes. Dots of fth1 phage (negative control vector), CD4 protein, and phages displaying the m1 and m2 peptides (see below) were applied to nitrocellulose filters. The filters were then incubated with gp120$_{451}$ or not, as indicated. Dots were then probed with a panel of defining mAbs (b12, b6, 17b, m14, 9G3 and CG10) or with CD4 as indicated and then allowed to react with HRP conjugated antibodies and developed for ECL. Note that m1 and m2 peptides induced CG10 binding without interfering with b12, b6 or m14 binding.

Evaluation of m1 Peptide/gp120 Complex Against a Defining Panel of gp120-Specific mAbs Because the CD4i conformation of gp120 can disrupt the integrity/accessibility of important neutralizing epitopes of gp120 [e.g. b12 (Xiang et al., 2002, supra)] the binding of a panel of neutralizing antibodies was tested. FIG. 4 shows results of testing a panel of 6 different anti-gp120 mAbs against the m1/gp120$_{451}$ complex. CG10 bound the complex as did mAb 17b, illustrating availability of the co-receptor binding site. Moreover, CD4 itself bound the m1/gp120 complex. However, this did not assure that CD4BS mAbs will continue to bind this CD4i conformation because there is not precise coincidence of the CD4 binding site itself and the CD4BS epitopes (see below and in T. Zhou et al., 2007, *Nature* 445:732-7, which discloses X-ray resolution of the structure of the epitope bound by mAb b12 epitope in a mutant gp120 that stabilized the structure via novel disulfide bonds).

Figure 5:
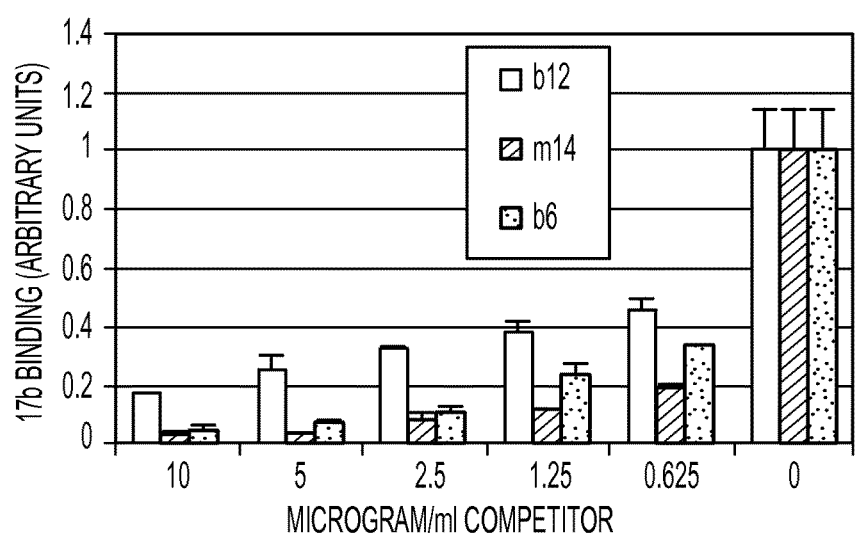
FIG. 5 shows that the b12 epitope is in close proximity to the epitope recognized by the 17b mAb. Competitive ELISA tests showed that gp120$_{451}$ bound biotinylated 17b mAb in the absence of competing antibody without the need for CD4 induction. Increasing concentrations of either b12, m14 or b6 mAbs inhibited binding of the biotinylated 17b mAb in ELISA.

As shown in FIG. 4, three competing neutralizing CD4BS mAbs (b12, b6 and m14) bind the m1/gp120 complex very well. As expected these mAbs did not bind a CD4/gp120 complex. Moreover, as is illustrated in FIG. 5 these antibodies actually compete against 17b mAb, demonstrating that the epitopes of 17b, b12, b6 and m14 are (a) in close proximity, (b) distinct and (c) do not coincide with the CD4 binding site itself (Bublil E M et al., 2006, *FASEB J.* 20:1762-74). Thus, according to the invention, this panel of mAbs serves as a "monitor" of the quality of the complexes to be used as immunogens.

EXAMPLE 5 m1 Variants Show Improved Affinity for gp120

Using random biased mutagenesis, an approach devised by one of the present inventors and applicable for peptide optimization using combinatorial phage display peptide libraries (Ophir, R & Gershoni, J M, 1995, *Protein Eng* 8:143-6), the inventors enhanced the affinity of m1 peptide for gp120 while maintaining the ability to induce the CD4i conformation as monitored by CG10 binding.

Figure 6:
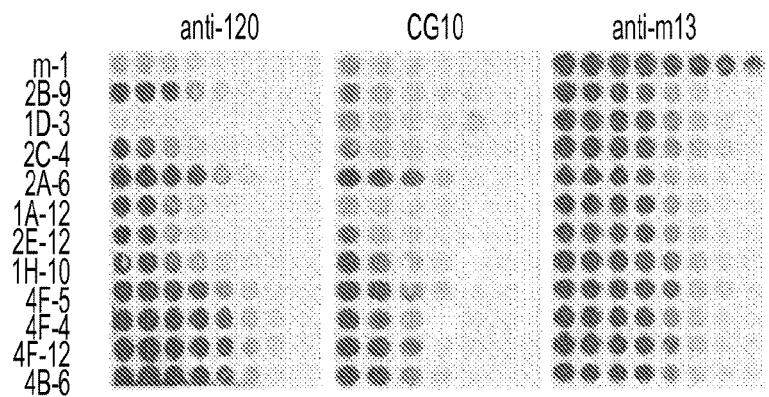
FIG. 6 shows that random biased mutagenesis of m1 peptide produced improved binders of gp120. A library of m1 peptide variants was produced using biased random mutagenesis and then panned against gp120 at sub-optimal conditions. Eleven peptide variants of m1 were cloned and tested for gp120 binding. Two-fold serial dilutions of the phages were used to create dot blot arrays which were incubated with gp120 and probed with either anti-gp120 mAb, CG10 or an anti-M13 (anti-phage) mAb to illustrate that similar concentrations of each phage were loaded at the various dilutions. Even though m1 was relatively overloaded, its binding to gp120 was barely detectable under conditions in which the "improved" m1-variants bound well.

Briefly, a novel m1-peptide-based phage display library was constructed using oligonucleotides produced by employing phosphoramidite precursors tainted with contaminating amounts of the "other three bases". Thus for example the stock bottle of G was contaminated with 3% each of A, T and C each. In this manner for every position requiring G in the oligonucleotide corresponding to the m1 sequence there was a 9% probability for a base replacement at this position. The library was then screened against gp120$_{451}$ at conditions of high stringency, and novel m1-peptide variants were isolated. As is illustrated in FIG. 6, numerous phages showed enhanced binding of gp120 under conditions where the original m1-peptide show barely detectable gp120 binding. Moreover, the modification of the peptides (Table 1, above) was accompanied by enhanced ability to induce the CG10 epitope. The peptides described in FIG. 6 are included in Table 1. Relatively few amino acid changes were introduced in the 11 modified m1-peptides (other than m2) shown. These changes are shown as underscored single letter amino acid codes.

Figure 7:
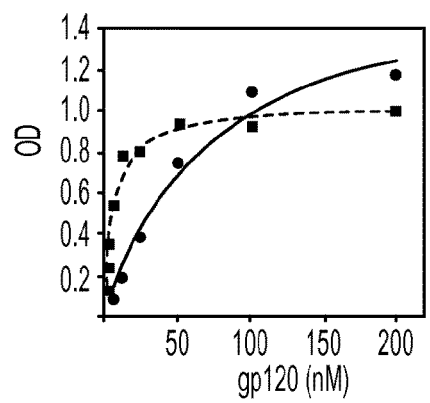
FIG. 7 shows comparison of binding of m1 and an improved variant of m1 to gp120. Quantitative ELISA was used to measure the binding of m1 peptide (circles) and an improved variant of m1 to gp120 (squares). The apparent affinity constants for gp120 binding to m1 and its variant were $6.9 \times 10^{-8}$M and $6.5 \times 10^{-9}$M respectively.
Figure 8:
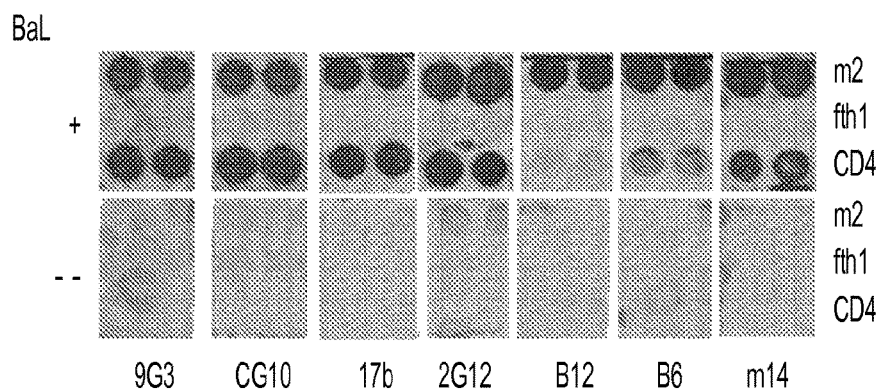
FIG. 8 shows that gp120 from HIV strain BaL (gp120$_{BaL}$) binds m2 peptide. Phages displaying the m2 peptide, fth1 negative control phages or CD4 protein were applied as dots to nitrocellulose filters and incubated with gp120$_{BaL}$ or not, as indicated. Each dot was applied in duplicate. The filters were probed with a panel of seven "defining" mAbs illustrating that m2 peptide induces both the CG10 and 17b epitopes in BaL-gp120 (BaL gp120 requires CD4 induction for 17b mAb. See, for example, Liao, H X et al., 2004, *J Virol* 78:5270-8). Moreover, the neutralizing epitopes of mAbs 2G12, b12, b6 and m14 were intact and available in the m2 captured gp120$_{BaL}$.

Quantitation of binding of m1-peptide and an improved peptide (designated m2) is described in FIG. 7. These results show attainment of a 10-fold increase in binding (compare $K_D$ values of 69.2 nM for m1 vs 6.5 nM for m2).

A second measure of "improved peptide" characteristics is the ability to bind gp120s derived from other HIV-1 isolates. (m1 was developed using $gp120_{451}$.) The preference was to identify a peptide that has the same type of effect on the BaL isolate of HIV-1 as does the m1-peptide for the 451 isolate. This is because $gp120_{BaL}$ has been found to be a preferred immunogen (Liao et al., supra). Results in FIG. 8 demonstrate that the m2-peptide binds $gp120_{BaL}$, induces CD4i epitopes, is able to bind CD4 itself and maintains the integrity of the CD4BS epitopes defined by mAbs b12, b6 and m14.

All references cited herein, including journal articles or abstracts, published or corresponding U.S. or foreign patent applications, issued U.S. or foreign patents, or any other references, are incorporated by reference herein in their entirety, including all data, tables, figures, and text presented in the cited references. Additionally, the contents of the references cited within the references cited herein are also incorporated by references in their entirety.

Reference to known method steps, conventional methods steps, known methods or conventional methods is not in any way an admission that any aspect, description or embodiment of the present invention is disclosed, taught or suggested in the relevant art.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A peptide that binds to human immunodeficiency virus type 1 (HIV-1) envelope protein gp120 and consists of a sequence of 8-20 amino acid residues comprising:
   (a) a core sequence Arg-Xaa$_1$-Asp-Leu-Pro-Xaa$_2$-Trp-Ala (SEQ ID NO:1) wherein Xaa$_1$ and Xaa$_2$ may be any amino acid, or
   (b) a peptide variant of SEQ ID NO:1 in which one of residues Arg, Asp, Leu, Pro, Trp and Ala is conservatively substituted.

2. A peptide according to claim 1 that, when bound to gp120, causes the gp120 to assume a CD4i conformation.

3. A peptide according to claim 1, that binds to gp120 while preserving binding of the gp120 to:
   (a) CD4 or a gp120-binding fragment or variant of CD4;
   (b) a mAb or other ligand specific for a an epitope of the CD4 binding site (a CD4BS epitope) of gp120.

4. A peptide according to any of claim 1, wherein Xaa$_1$ is Arg, Lys, Ser, Asn or Leu and Xaa$_2$ is Gln, Glu, Lys, Leu, Asp, or Asn.

5. A peptide according to claim 1, that, when complexed with
   (i) said gp120; or
   (ii) a fragment or variant of said gp120 that binds the peptide, binds to monoclonal antibody 17b and/or CG10.

6. A peptide according to claim 1, the sequence of which is (SEQ ID NO: 16)
Cys-Xaa$_3$-Arg-Xaa$_1$-Asp-Leu-Pro-Xaa$_2$-Trp-Ala-Xaa$_4$-Xaa$_5$-Xaa$_6$-Cys wherein
Xaa$_1$ is Arg, Ser or Asn
Xaa$_2$ is Gln, Lys, Leu, Asp or Glu;
Xaa$_3$ is Asp, Gly or Ala
Xaa$_4$ is Lys, Ile, Met or Asn;
Xaa$_5$ is Arg or Ser; and
Xaa$_6$ is Glu, Ala or Val.

7. A peptide according to claim 1, which is s selected from the group consisting of:

(SEQ ID NO: 3)
(a) Cys-Asp-Arg-Arg-Asp-Leu-Pro-Gln-Trp-Ala-Lys-Arg-Glu-Cys (SEQ ID NO: 4)
(b) Cys-Asp-Arg-Ser-Asp-Leu-Pro-Gln-Trp-Ala-Lys-Arg-Ala-Cys;

(SEQ ID NO: 5)
(c) Cys-Gly-Arg-Arg-Asp-Leu-Pro-Lys-Trp-Ala-Met-Arg-Glu-Cys;

-continued (d) Cys-Asp-Arg-Arg-Asp-Leu-Pro-Glu-Trp-Ala-Lys-Arg-Glu-Cys; (SEQ ID NO: 6)

(e) Cys-Asp-Arg-Arg-Asp-Leu-Pro-Gln-Trp-Ala-Ile-Arg-Glu-Cys; (SEQ ID NO: 7)

(f) Cys-Ala-Arg-Arg-Asp-Leu-Pro-Leu-Trp-Ala-Lys-Arg-Glu-Cys; (SEQ ID NO: 8)

(g) Cys-Asp-Arg-Asn-Asp-Leu-Pro-Gln-Trp-Ala-Lys-Ser-Ala-Cys; (SEQ ID NO: 9)

(h) Cys-Asp-Arg-Arg-Asp-Leu-Pro-Gln-Trp-Ala-Asn-Arg-Ala-Cys; (SEQ ID NO: 10)

(i) Cys-Asp-Arg-Arg-Asp-Leu-Pro-Gln-Trp-Ala-Met-Ser-Ala-Cys; (SEQ ID NO: 11)

(j) Cys-Asp-Arg-Arg-Asp-Leu-Pro-Gln-Trp-Ala-Ile-Ser-Ala-Cys; (SEQ ID NO: 12)

(k) Cys-Asp-Arg-Ser-Asp-Leu-Pro-Gln-Trp-Ala-Ile-Ser-Ala-Cys; (SEQ ID NO: 13)

(l) Cys-Asp-Arg-Arg-Asp-Leu-Pro-Gln-Trp-Ala-Ile-Ser-Val-Cys; (SEQ ID NO: 14)
and (m) Cys-Asp-Arg-Arg-Asp-Leu-Pro-Asp-Trp-Ala-Ile-Arg-Ala-Cys (SEQ ID NO: 15)

and (m) Cys-Asp-Arg-Arg-Asp-Leu-Pro-Asp-Trp-Ala-Ile-Arg-Ala-Cys (SEQ ID NO:15)

8. A cyclic peptide that is the peptide according to claim 6, wherein the two Cys residues are linked in a disulfide bond.

9. A peptide according to claim 1, the length of which is 12-20 residues, wherein the sequence further comprises a first and a second cyclizing amino acid that (i) can bond to one another to cyclize, and (ii) are separated from one another by at least 10 residues.

10. A linear oligomer or multimer that comprises between about two and about 20 repeats of the peptide of claim 1.

* * * * *